United States Patent
Golestani Rad et al.

(10) Patent No.: US 12,373,945 B2
(45) Date of Patent: Jul. 29, 2025

(54) METHOD AND SYSTEM TO PREDICT RF HEATING OF MEDICAL IMPLANTS

(71) Applicant: Northwestern University, Evanston, IL (US)

(72) Inventors: Laleh Golestani Rad, Wilmette, IL (US); Behzad Elahi, Chicago, IL (US); Jasmine Christina Vu, Evanston, IL (US)

(73) Assignee: Northwestern University, Evanston, IL (US)

( * ) Notice: Subject to any disclaimer, the term of this patent is extended or adjusted under 35 U.S.C. 154(b) by 481 days.

(21) Appl. No.: 17/918,260

(22) PCT Filed: Apr. 22, 2021

(86) PCT No.: PCT/US2021/028558
§ 371 (c)(1),
(2) Date: Oct. 11, 2022

(87) PCT Pub. No.: WO2021/216818
PCT Pub. Date: Oct. 28, 2021

(65) Prior Publication Data
US 2023/0137794 A1 May 4, 2023

Related U.S. Application Data

(60) Provisional application No. 63/013,704, filed on Apr. 22, 2020.

(51) Int. Cl.
*G06T 7/00* (2017.01)
*A61N 1/05* (2006.01)

(52) U.S. Cl.
CPC .......... *G06T 7/0012* (2013.01); *A61N 1/0529* (2013.01); *A61N 1/0551* (2013.01);
(Continued)

(58) Field of Classification Search
None
See application file for complete search history.

(56) References Cited

U.S. PATENT DOCUMENTS 9,061,132 B1  6/2015 Zweber et al.
2010/0106214 A1  4/2010 Min
(Continued)

OTHER PUBLICATIONS

The International Search Report and the Written Opinion issued on Aug. 6, 2021 for international patent application No. PCT/US2021/028558; pp. 1-7.

*Primary Examiner* — Mark R Milia
(74) *Attorney, Agent, or Firm* — Bell & Manning, LLC

(57) ABSTRACT

A system to predict heating in implants includes a memory configured to store an image of a patient. The image includes a medical implant of the patient. The system also includes a processor operatively coupled to the memory and configured to determine an implant trajectory of the medical implant. The processor is also configured to determine a tangential component of an electric field that is incident upon the medical implant at a plurality of locations along the implant trajectory. The processor is further configured to determine, based on the implant trajectory and the tangential component of the electric field at each of the plurality of locations, a specific absorption rate of radiofrequency (RF) energy associated with the medical implant.

20 Claims, 25 Drawing Sheets

(52) U.S. Cl.
CPC ............... *G06T 2207/20081* (2013.01); *G06T 2207/20084* (2013.01)

(56) References Cited

U.S. PATENT DOCUMENTS

| | | |
|---|---|---|
| 2010/0168821 A1 | 7/2010 | Johnson et al. |
| 2010/0217262 A1 | 8/2010 | Stevenson et al. |
| 2014/0288619 A1 | 9/2014 | Johnson et al. |
| 2016/0344240 A1 | 11/2016 | Yeh et al. |
| 2020/0393526 A1* | 12/2020 | Wang ................ G01R 33/5611 |

* cited by examiner

| | Num Tets. | Min edge Length (mm) | Max edge Length (mm) | RMS edge Length (mm) | Min tet. Vol. (mm³) | Max tet. Vol. (mm³) | Mean tet. Vol. (mm³) | Std. Devn. (Vol.) (mm³) |
|---|---|---|---|---|---|---|---|---|
| DBS lead | 150366 | 0.07 | 0.50 | 0.42 | $5.33 \times 10^{-8}$ | 0.018 | 0.002 | 0.002 |
| DBS insulation | 395091 | 0.06 | 0.50 | 0.38 | $7.69 \times 10^{-8}$ | 0.016 | 0.002 | 0.001 |
| Head | 1071444 | 0.09 | 10 | 3.88 | $1.52 \times 10^{-7}$ | 84.75 | 4.78 | 7.97 |
| SAR box | 48327 | 0.22 | 2 | 1.44 | $1.22 \times 10^{-4}$ | 0.66 | 0.16 | 0.11 |

| Parts | Num of Tets | Min edge length (mm) | Max edge length (mm) | RMS edge length (mm) |
|---|---|---|---|---|
| Human body | 276366 | 0.30 | 26.68 | 12.62 |
| Cubic region | 406625 | 0.19 | 2.46 | 1.57 |
| Insulation | 369495 | 0.11 | 2.00 | 0.58 |
| Wire | 208258 | 0.03 | 1.23 | 0.42 |
| Coil | 38706 | 9.84 | 501.79 | 64.35 |

Fig. 12

METHOD AND SYSTEM TO PREDICT RF HEATING OF MEDICAL IMPLANTS

CROSS-REFERENCE TO RELATED APPLICATION

The present application is a National Stage of International Application No. PCT/US21/28558, filed Apr. 22, 2021, which claims the priority benefit of U.S. Provisional Patent App. No. 63/013,704, filed Apr. 22, 2020, the entire contents of both of which are incorporated herein by reference.

REFERENCE TO GOVERNMENT RIGHTS

This invention was made with government support under EB021320 awarded by The National Institutes of Health (NIH). The government has certain rights in the invention.

BACKGROUND

The market for medical implantable electronic devices is rapidly growing. In the field of neurostimulation devices alone, the market is projected to grow at a steep rate of 12% per year, and is estimated to reach $9 billion by 2024. In addition to neurostimulation devices such as deep brain stimulators, electronic medical implants can also include spinal cord stimulators, vagus nerve stimulators, cardiovascular pacemakers and defibrillators, etc. As with most electronic devices, electronic medical implants can be adversely affected by electrical signals in the environment. For example, many imaging techniques expose patients to electrical signals and radiation, which can potentially interact with any medical implants embedded in the patient. Magnetic resonance imaging (MRI), which is a popular imaging technique that is performed more than 33 billion times in the US every year, is an example of such an imaging technique.

SUMMARY

An illustrative system to predict heating in implants includes a memory configured to store an image of a patient. The image includes a medical implant of the patient. The system also includes a processor operatively coupled to the memory and configured to determine the trajectory of the medical implant. The processor is also configured to determine a tangential component of an electric field that is incident upon the medical implant at a plurality of locations along the implant trajectory. The processor is further configured to determine, based on the implant trajectory and the tangential component of the electric field at each of the plurality of locations, a specific absorption rate of radiofrequency (RF) energy associated with the medical implant. The processor can additionally or alternatively determine a temperature rise ($\Delta T$) of the medical implant. The RF energy and temperature rise can result from a magnetic resonance imaging (MRI) procedure, or any other type of procedure in which radiation contacts the medical implant.

An illustrative method for predicting heating in implants includes storing, in a memory of a computing system, an image of a patient, where the image includes a medical implant of the patient. The method also includes determining, by a processor operatively coupled to the memory, an implant trajectory of the medical implant. The method also includes determining, by the processor, a tangential component of an electric field that is incident upon the medical implant at a plurality of locations along the implant trajectory. The method further includes determining, by the processor and based on the implant trajectory and the tangential component of the electric field at each of the plurality of locations, a specific absorption rate of radiofrequency (RF) energy associated with the medical implant. The processor can additionally or alternatively determine a temperature rise ($\Delta T$) of the medical implant. The RF energy and temperature rise can result from a magnetic resonance imaging (MRI) procedure, or any other type of procedure in which radiation contacts the medical implant.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 12 includes a table that gives the mesh statistics for a representative simulation in accordance with an illustrative embodiment.

DETAILED DESCRIPTION

Figure 1B:
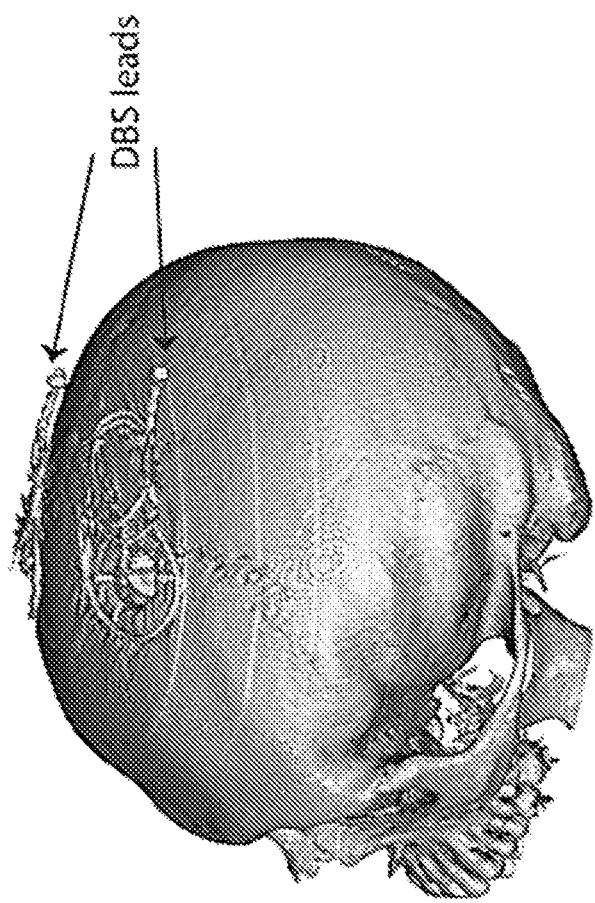
FIG. 1B is a second 3D surface rendered view of CT images of a patient with implanted DBS leads in accordance with an illustrative embodiment.
Figure 1A:
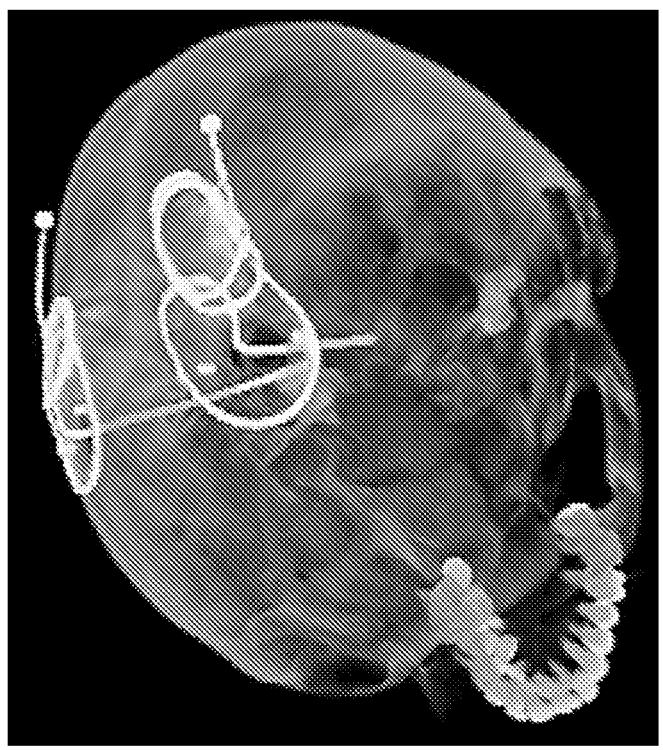
FIG. 1A is a first 3D surface rendered view of CT images of a patient with implanted DBS leads in accordance with an illustrative embodiment.
Figure 1D:
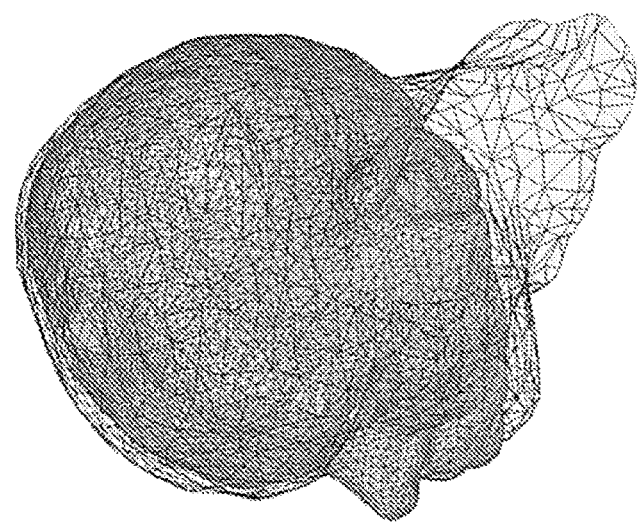
FIG. 1D depicts alignment of a 3D model of the patient's head with the homogeneous multimodal imaging-based detailed anatomical (MIDA) model in accordance with an illustrative embodiment.
Figure 1C:
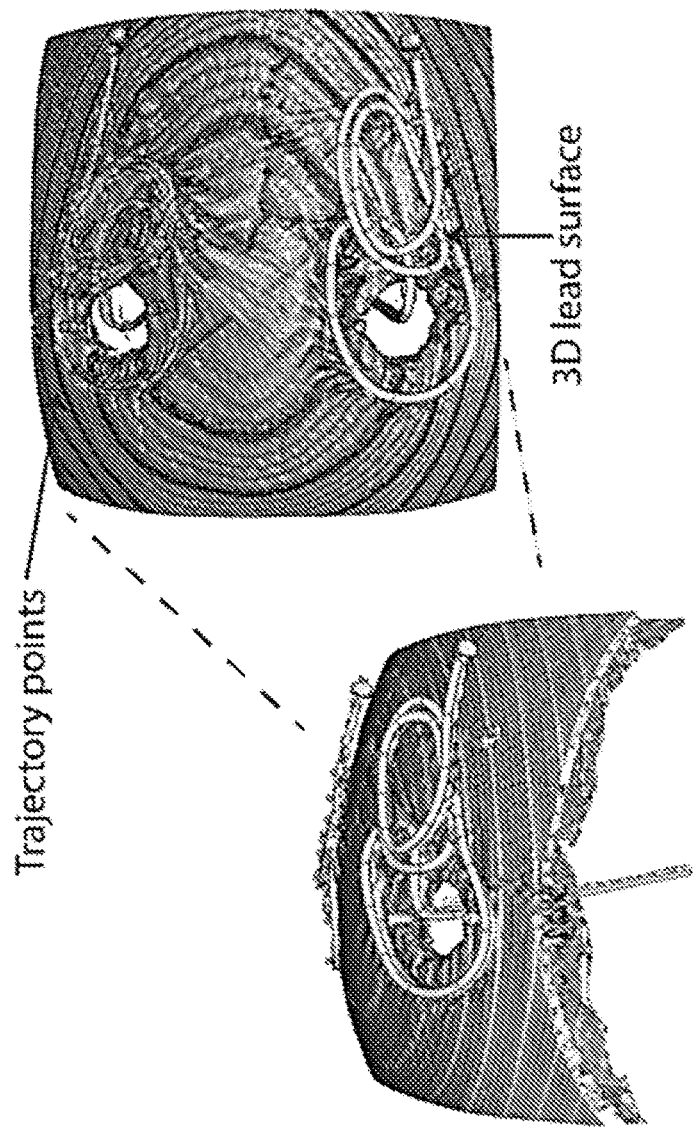
FIG. 1C shows manual segmentation of lead trajectories for the implants in accordance with an illustrative embodiment.
Figure 1F:
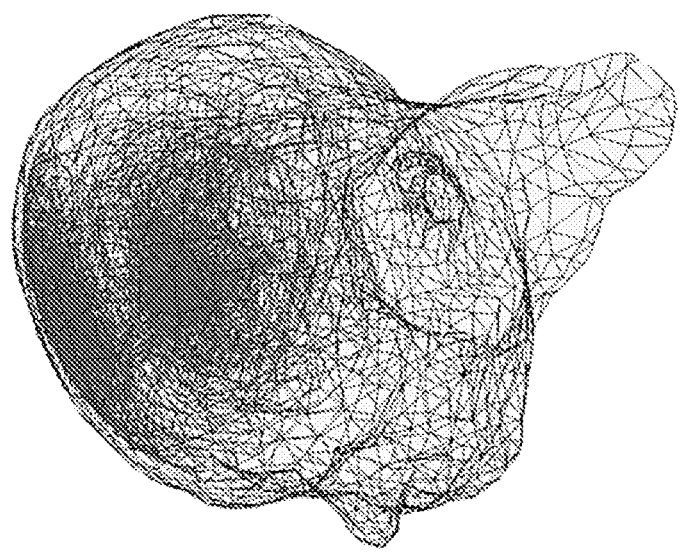
FIG. 1F depicts a superposition of all 83 patient-derived and 177 artificial lead trajectories in the homogeneous MIDA model in accordance with an illustrative embodiment.
Figure 1E:
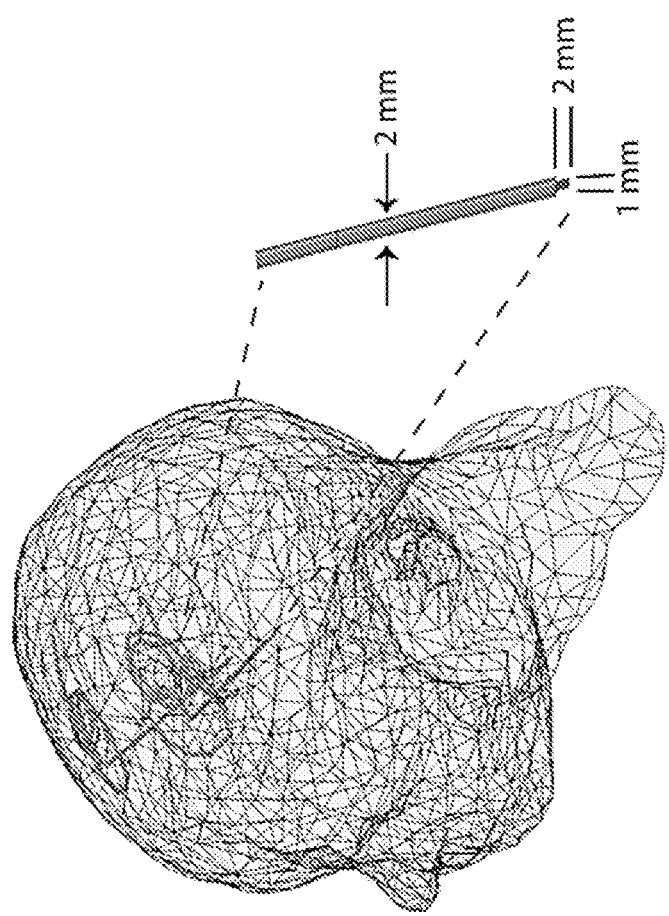
FIG. 1E shows how lead trajectories were reconstructed as simplified lead models represented by a conductive wire embedded with a urethane insulating sheath in accordance with an illustrative embodiment.

Radio frequency (RF) heating refers to an electrical phenomenon in which electromagnetic (EM) signals and radiation passing through an object causes the object to heat up. The heating occurs due to the interaction of the electrical and magnetic fields from the EM signals with certain metals, dielectric materials, etc. The RF heating of implanted medical devices can result in patient injury, and is an important consideration for medical professionals when determining whether a patient can be subjected to imaging techniques such as magnetic resonance imaging (MRI). As a result, the risk of RF heating in implants such as deep brain stimulators, spinal cord stimulators, and cardiovascular devices prevents hundreds of thousands of patients from receiving life-saving diagnostic MRI examinations each year.

Medical device companies have spent millions of dollars in efforts to i) develop new medical implant devices with a reduced risk of RF heating, and ii) perform safety tests to obtain Food and Drug Administration (FDA) approval for the MRI-conditional labeling of these devices. Traditional techniques to determine the amount of RF heating that will result in an implant involve performing full-wave electromagnetic (EM) simulations to determine the specific absorption rate (SAR) of EM energy, and/or resultant temperature rise in the tissue surrounding the implant. Such techniques are costly and time consuming. For example, a complete full-wave EM simulation typically involves the use of a commercial EM solver to perform millions of simulations that model all possible implant trajectories and predict a worst case implant heating scenario for each possible trajectory. A single license to use such an EM solver (e.g., ANSYS Electronic Desktop) can cost several thousand dollars. Usually, up to several hundred licenses are needed to perform parallel simulations that allow for completion of an MRI RF safety assessment in a timely manner. Smaller companies are therefore often deterred from conducting these safety studies due to the associated high costs. Additionally, conducting a full-wave simulation consumes a considerable amount of time (e.g., 4-7 hours) and computer memory (200-500 Gigabytes (GB)) of random access memory (RAM)). Using these traditional techniques, companies often spend between 3-4 years on studies and simulations in an effort to obtain FDA labeling for each new medical implant device.

The methods and systems described herein are significantly more cost effective and less time-consuming than traditional techniques. Specifically, described herein is an artificial intelligence (AI)-assisted ultra-fast methodology to predict the amount of RF heating in the tissue surrounding the implants having an arbitrary configuration inside different types of MRI scanners. The proposed methods and systems do not use a full-wave simulation, as in traditional techniques. Rather, the proposed systems and methods involve the use of newly discovered relationships between implants and radiation to train an Artificial Neural Network (ANN) or other machine learning system/algorithm to predict RF heating. After the ANN network or other machine learning system/algorithm is trained, subsequent simulations will take only a few seconds to complete, which dramatically reduces the time and cost associated with the process. This allows medical device companies to acquire FDA labeling for their MR-conditional implants with a significantly reduced cost and in a substantially shorter amount of time. Considering the rapid spread of high-field MRI scanners for which there are no MR-conditional implantable devices available yet, and the steep growth in use of electronic medical implants such as neuromodulation devices and cardiovascular implants, there is a significant need for this technology.

It is well established that the trajectory of a conductive wire implant inside the body significantly affects its RF heating, and that RF heating is a complex phenomenon in which small changes in trajectory of the wire can cause sizeable changes in the specific absorption rate (SAR) of the implant. The SAR is a measure of the amount of RF power absorbed per unit of mass of an object, and is typically measured in Watts/kilogram (W/kg). While researching the relationship between device trajectory and RF heating, the inventors discovered that the value of a tangential component of an incident electric field along the trajectory of a wire implant plays a decisive role in determining the RF heating at the tip of implant. As a result, the incident electric field of an MRI scanner or other imaging device is considered to be the signature of the scanner or imaging device, and this signature is independent of implant trajectory. By exploiting these relationships, it becomes possible to predict the RF heating of an implant by knowing only its trajectory in the body and the signature of the RF coil that emits the radiation.

The trajectory of a metallic implant inside the body of a patient can be effectively extracted from computed tomography (CT) images of the patient. Alternatively, a different method may be used such as x-ray imaging, etc. The RF signature of the RF coil in an MRI device can be estimated with good accuracy via modeling. An ANN or other machine learning system/algorithm can then be trained using these two inputs (implant trajectory and RF coil signature). Once trained, the ANN or other machine learning system/algorithm can be used to predict the RF heating of an implant that would be caused by the MIll device without the need to run a full-wave simulation. This will reduce the computation time by a factor of 100-1000.

To validate the proposed techniques, deep brain stimulation (DBS) lead models with patient-derived trajectories were constructed based on postoperative CT images of patients with DBS implants. In total, 83 patient-derived DBS lead models with unique trajectories were reconstructed from medical images. The DBS leads were identified in postoperative CT images using 3D Slicer 4.10.2 visualization software. In alternative embodiments, different visualization software may be used. Once the lead artifacts were identified, preliminary 3D surfaces of lead trajectories were constructed, and the corresponding coordinates of points along the lead trajectories were extracted. A triangulated surface model of the patient's head was also created from CT images and manually aligned to a standard homogeneous head model ($\sigma$=0.49 S/m, $\varepsilon_r$=66.34) based on the Multimodal Imaging-Based Detailed Anatomical (MIDA) human head and neck model via rigid transformation/registration (translation and scaling only, 6 degrees of freedom). The same transformation was then applied to the lead trajectories to allow for anatomically representative positioning of the leads in the homogeneous head model.

The extracted lead coordinates were used to reconstruct models of simplified DBS leads comprised of a conductive wire ($\sigma$=4×10$^6$ S/m, diameter=1 mm) embedded within a urethane insulation ($\sigma$=0 S/m, $\varepsilon_r$=3.5, diameter=2 mm) with a 2 mm exposed tip. All lead models were 40 cm in length, consistent with the lengths of Abbott lead models 6172 and 6173. Each constructed model was inspected and adjusted if necessary, to ensure there were no self-intersections between the conductive wire and the insulation. In alternative embodiments, a different overall length and/or exposed lead tip length may be used to assess different types of leads.

FIG. 1 depicts various operations performed in the image segmentation and model creation. Specifically, FIG. 1A is a first 3D surface rendered view of CT images of a patient with implanted DBS leads in accordance with an illustrative embodiment. FIG. 1B is a second 3D surface rendered view of CT images of a patient with implanted DBS leads in accordance with an illustrative embodiment. FIG. 1C shows manual segmentation of lead trajectories for the implants in accordance with an illustrative embodiment. To perform the segmentation, preliminary 3D surfaces of lead trajectories were created, and points along lead trajectories were extracted using visualization software. FIG. 1D depicts alignment of a 3D model of the head of the patient with the homogeneous MIDA model in accordance with an illustrative embodiment. FIG. 1E shows how lead trajectories were reconstructed as simplified lead models represented by a conductive wire embedded with a urethane insulating sheath in accordance with an illustrative embodiment. The simplified lead model has a 2 mm exposed tip, as shown. FIG. 1F depicts a superposition of all 83 patient-derived and 177 artificial lead trajectories in the homogeneous MIDA model in accordance with an illustrative embodiment.

The analysis reflected in FIG. 1 demonstrates that there is substantial patient-to-patient variation in the extracranial trajectory of DBS leads, primarily reflecting the practice style of the surgeon. To account for this variation and to include trajectories that are known to generate worst-case RF heating during DBS imaging, the original dataset was augmented with the 177 artificial DBS lead trajectories referenced in FIG. 1F. To construct these artificial DBS lead trajectories, the coordinates of points corresponding to the intracranial portions of artificial trajectories—the segment from the lead's tip to the exit point on the skull (~7-8 cm)—were extracted from five actual patients. Subsequently, a trajectory line for the extracranial region was manually drawn and connected to one of the intracranial regions. Trajectory lines for the leads were exported to a computing system (e.g., ANSYS HFSS) to construct the conductive wire and insulation as described above.

Once the image segmentation and modeling was complete, electromagnetic simulations were implemented. A numerical model of a 16-rung low-pass birdcage head coil (diameter=356 mm, length=292 mm) tuned to the operating frequency of 64 MHz for 1.5 T MM with quadrature excitation was loaded with the homogeneous head model and lead models for simulations. A fixed voltage of 100 V was applied to each port of the coil in each simulation, generating a $B_1^+$ of approximately 1.1 microTesla (µT) on a central transverse plane passing through the center of the head. The 1gSAR$_{max}$ was calculated in a 20 mm×20 mm×20 mm cubic region surrounding each lead-tip using the SAR calculation module incorporated in ANSYS HFSS per the IEEE STD P1 528.4 recommendation. These maximum SAR values represent the simulated ground-truth SAR values used to train the algorithm. In alternative embodiments, a different operating frequency, fixed voltage, and/or cubic region size may be used.

Simulations were performed with an adaptive mesh scheme. A fine resolution was applied to the leads with a maximum tetrahedral mesh edge length of 0.5 mm. Additionally, the 20 mm×20 mm×20 mm cubic region surrounding the lead-tip had a maximum tetrahedral mesh edge length of 2 mm. Iterative simulations were completed until the maximum difference in S-parameter values, $\Delta S$, no longer exceeded the limit of 0.02. All simulations converged within 3 adaptive passes.

Figure 2B:
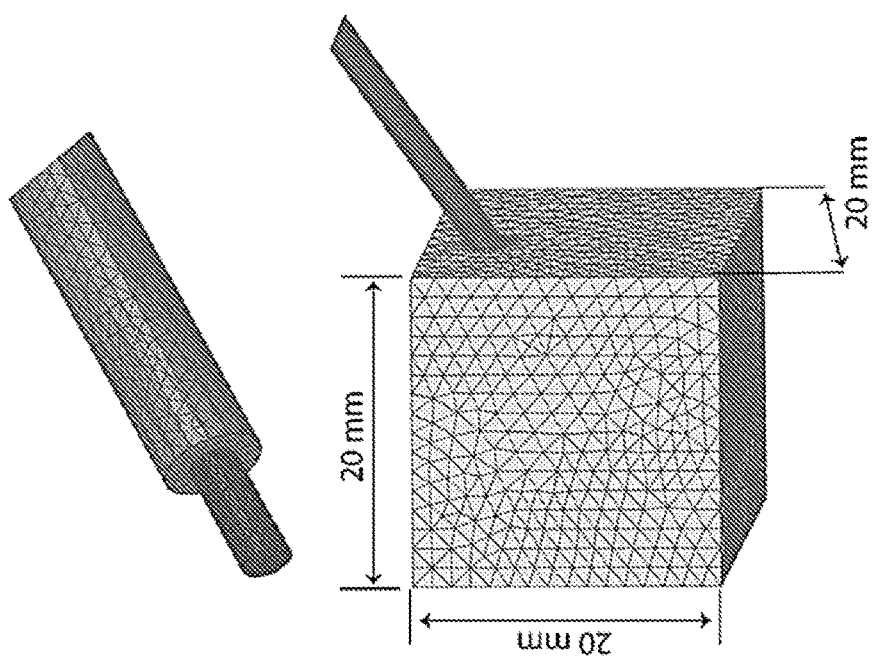
FIG. 2B shows example meshes of a lead (insulating sheath and conductive wire) and the region surrounding the lead tip in accordance with an illustrative embodiment.
Figure 2A:
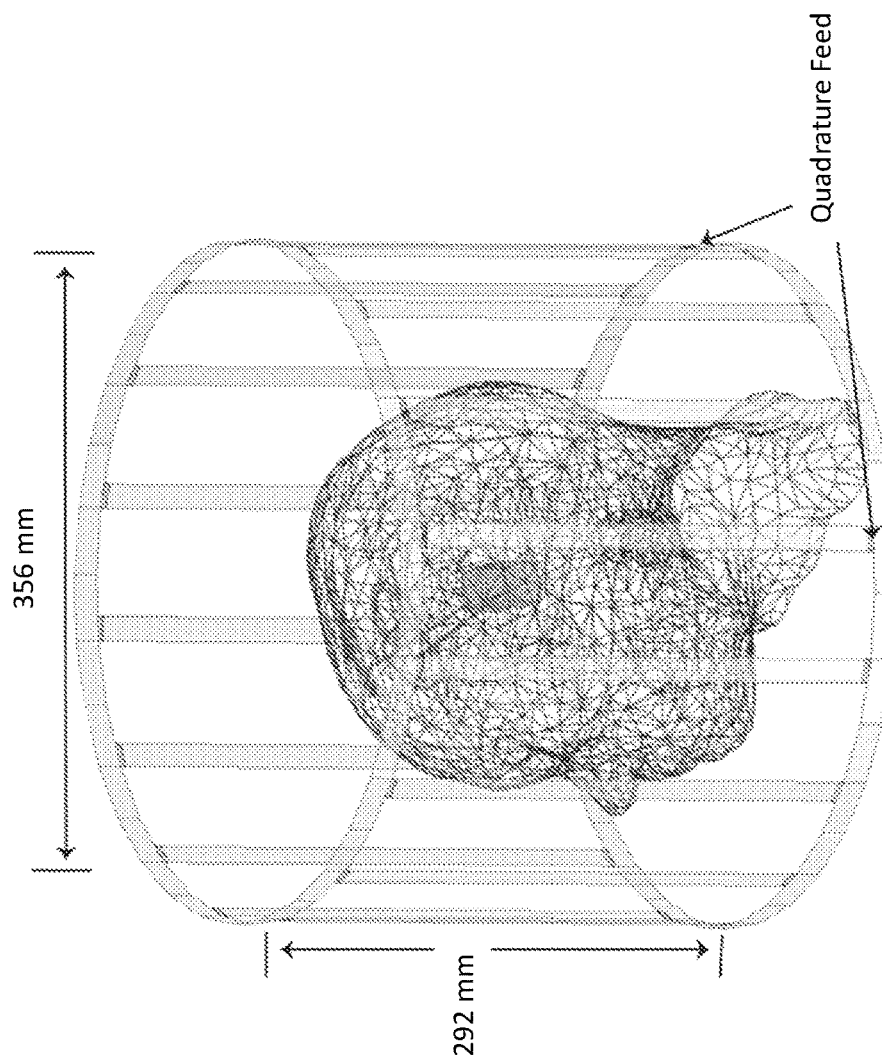
FIG. 2A depicts the position of the MIDA head model and two example leads in a birdcage MRI head coil in accordance with an illustrative embodiment.
Figures 2C, 2D:
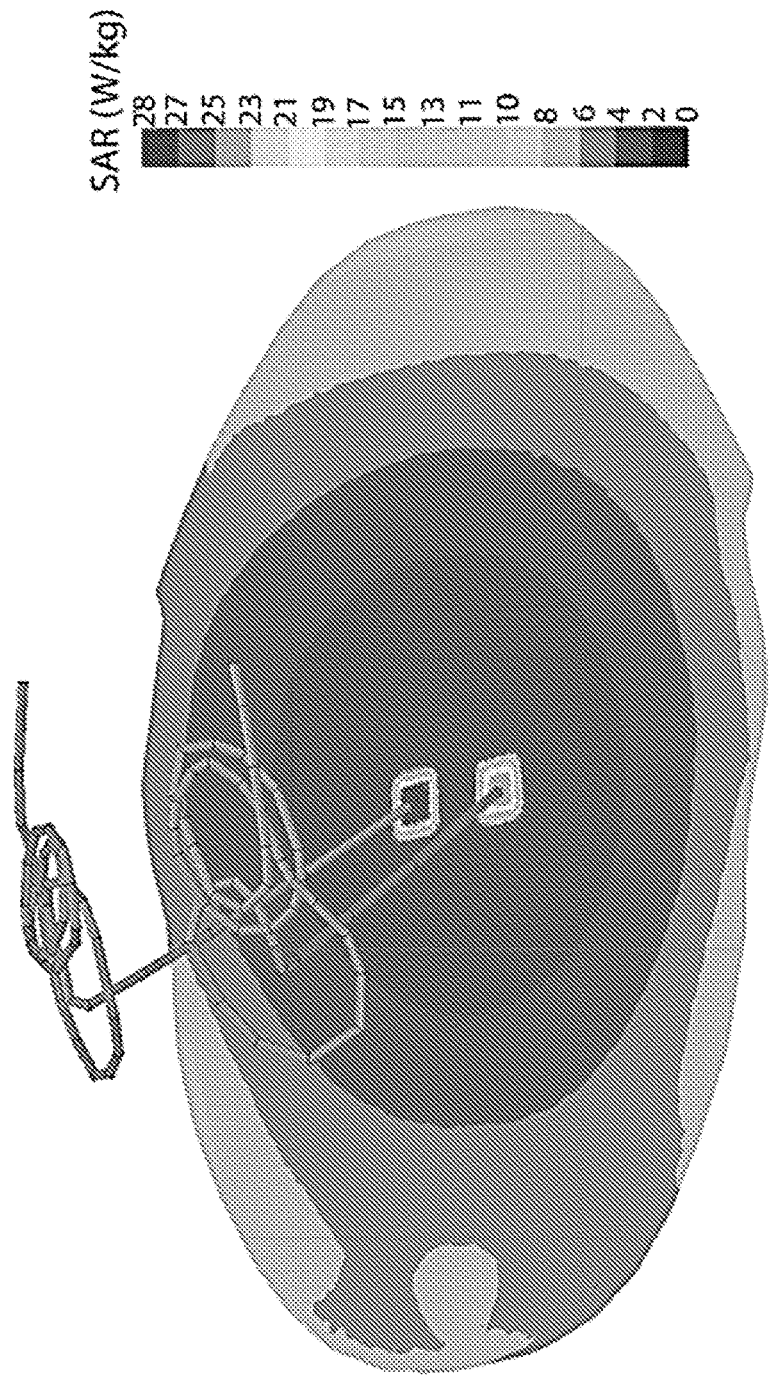
FIG. 2C shows maximum 1 g-averaged specific absorption rate (SAR) ($1gSAR_{max}$) displayed on an axial plane intersecting the lead-tips in accordance with an illustrative embodiment.
FIG. 2D is a table that shows details of mesh statistics for the example simulation in accordance with an illustrative embodiment.

FIG. 2 depicts details of the simulation setup and mesh statistics. FIG. 2A depicts the position of the MIDA head model and two example leads in a birdcage MRI head coil in accordance with an illustrative embodiment. Using this setup, the $1gSAR_{max}$ was calculated in the 20 mm×20 mm×20 mm region surrounding the tip of the lead. FIG. 2B shows example meshes of a lead (insulating sheath and conductive wire) and the region surrounding the lead tip in accordance with an illustrative embodiment. FIG. 2C shows 1 g-averaged SAR displayed on an axial plane intersecting the lead-tips in accordance with an illustrative embodiment. FIG. 2D is a table that shows details of mesh statistics for the example simulation in accordance with an illustrative embodiment.

To determine the incident electric field distribution along each lead trajectory, EM simulations were performed once with the head coil loaded with the homogeneous head model without the implanted leads. The tangential component of the incident electric field along each lead trajectory at a certain time point was then calculated and sampled at 5 mm increments along the length of each lead (for a total of 80 $E_{tan}$ values), and a subset of these values were used as input features of the deep learning algorithm, as depicted in FIG. 3.

Figure 3A:
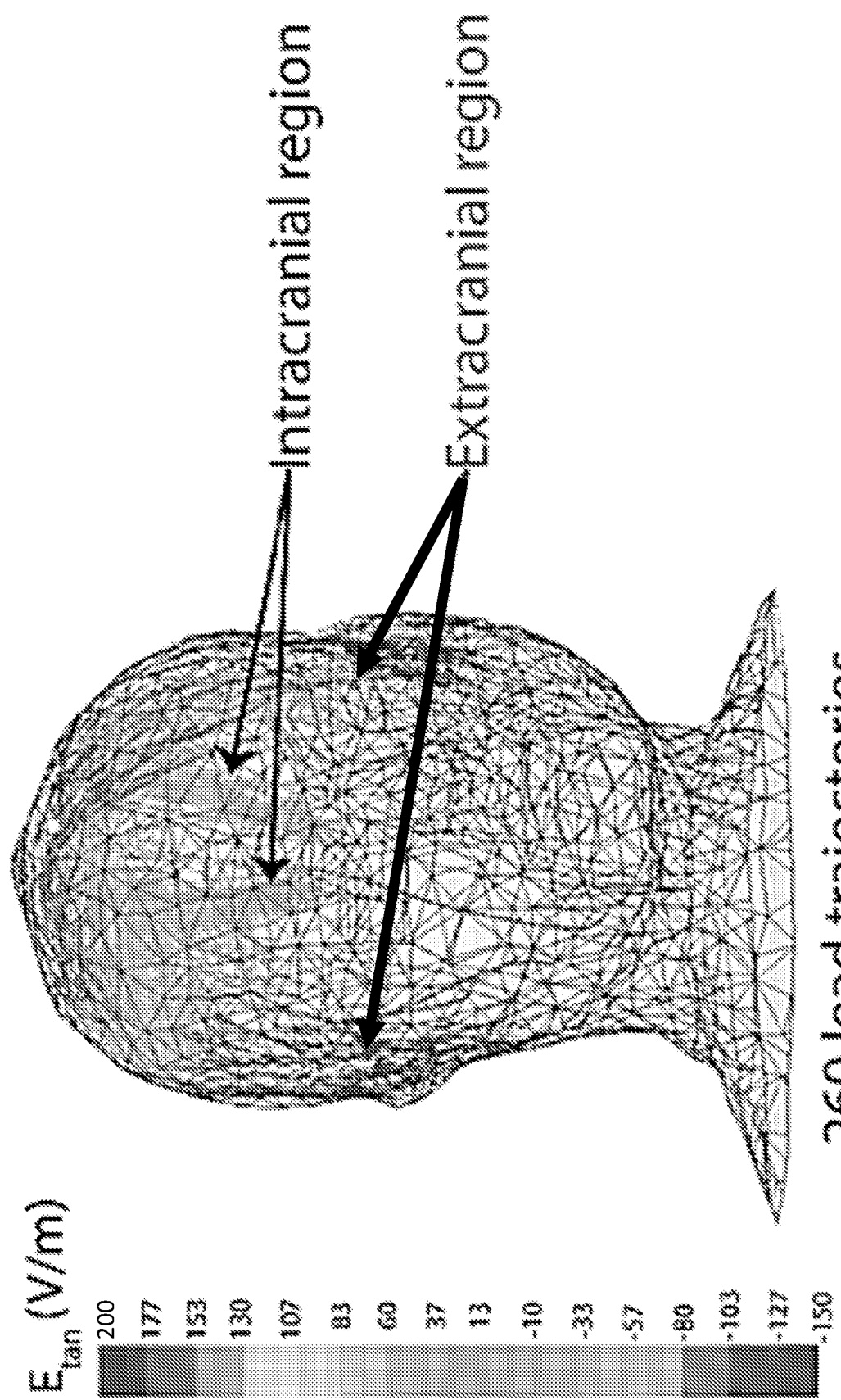
FIG. 3A depicts the superposition of incident electric field ($E_{tan}$) distributions along different lead trajectories in the homogeneous MIDA model in accordance with an illustrative embodiment.
Figure 3B:
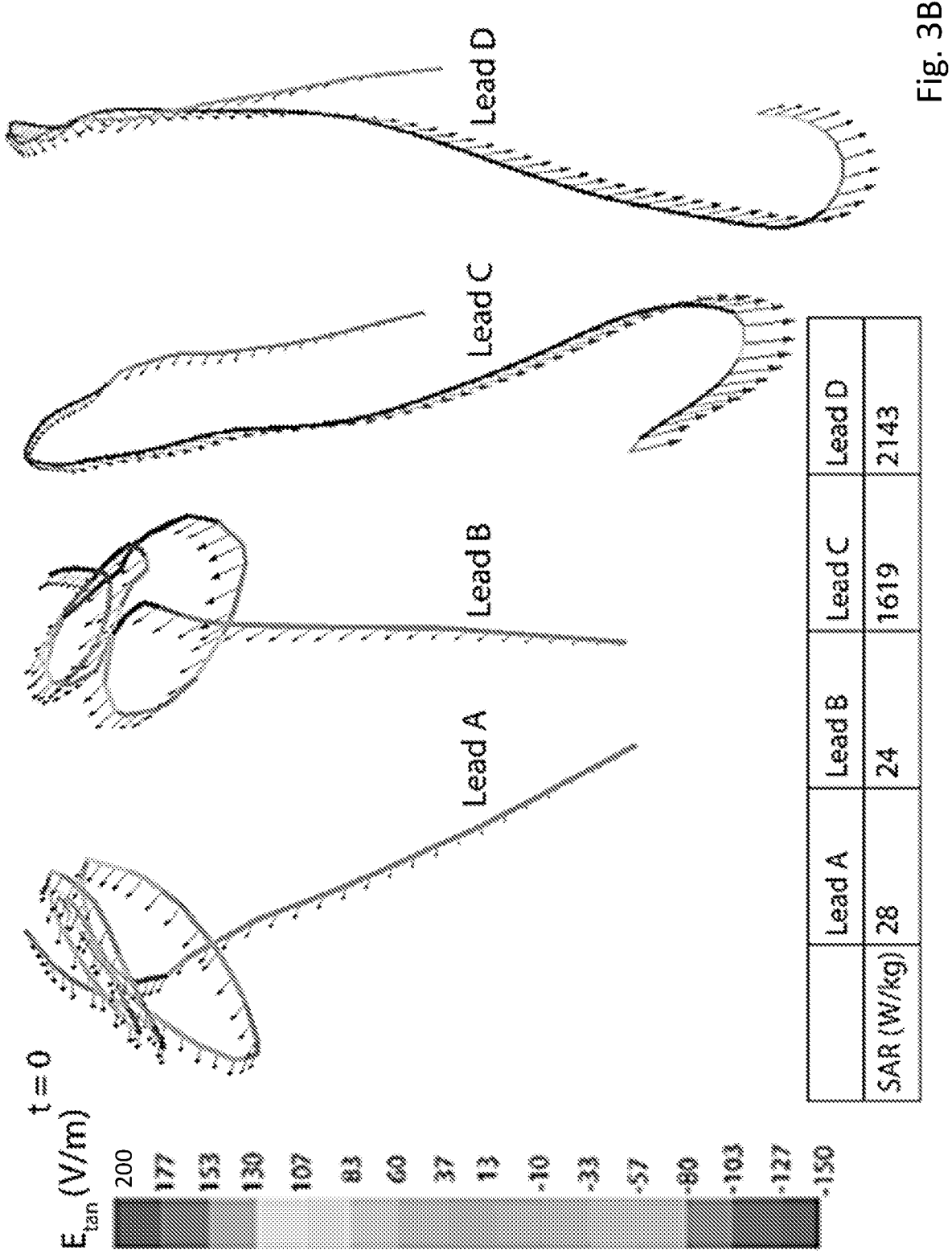
FIG. 3B depicts the distribution of $E_{tan}$ and the incident electric field (arrows) for lead trajectories that demonstrate low and high $1gSAR_{max}$ values in accordance with an illustrative embodiment.
Figure 3C:
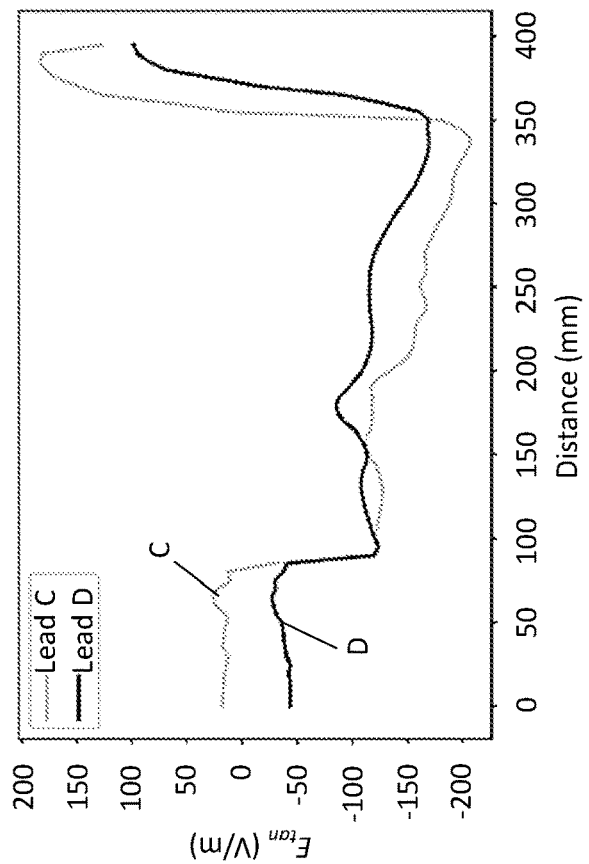
FIG. 3C shows the evolution of $E_{tan}$ along the length of the leads at t=0 in accordance with an illustrative embodiment.
Figure 3C:
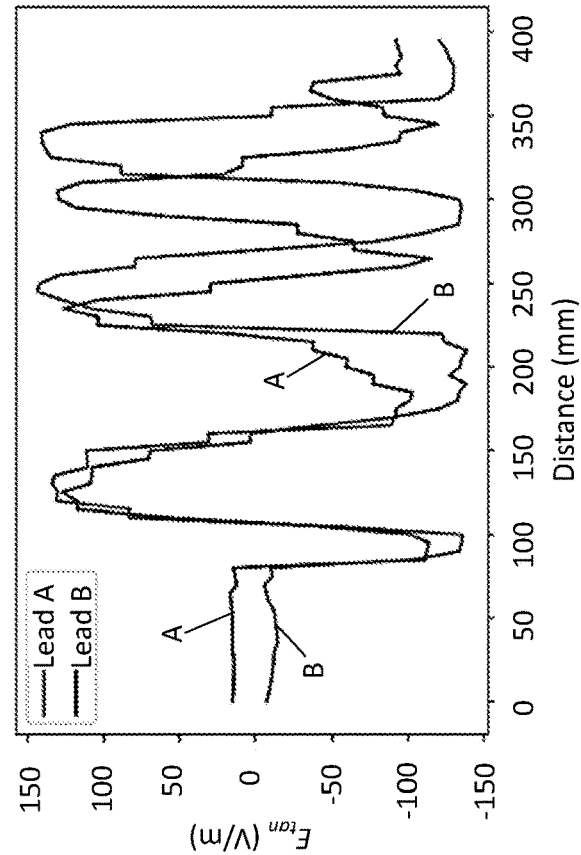

FIG. 3A depicts the superposition of incident electric field ($E_{tan}$) distributions along different lead trajectories in the homogeneous MIDA model in accordance with an illustrative embodiment. Similar $E_{tan}$ values were observed along the intracranial regions across lead trajectories. FIG. 3B depicts the distribution of $E_{tan}$ and the incident electric field (arrows) for lead trajectories that demonstrate low and high $1gSAR_{max}$ values in accordance with an illustrative embodiment. FIG. 3C shows the evolution of $E_{tan}$ along the length of the leads at t=0 in accordance with an illustrative embodiment.

The $E_{tan}$ distribution along the DBS lead depends on the orientation of the incident electric field with respect to the lead trajectory. It can be observed from FIG. 3 that the intracranial trajectories of all leads follow a similar path from the target nucleus (e.g., subthalamic nucleus) to the entry point on the skull determined via a standard surgical approach, which is typically completed during surgical planning. Thus, $E_{tan}$ values were highly similar for the intracranial region across different lead trajectories. For this reason, from the 80 $E_{tan}$ values that were originally sampled for each lead, only values pertaining to the extracranial region were included as features. Each extracranial $E_{tan}$ value served as an individual feature for a total of 63 features used in the predictive model. Lead trajectories were randomly selected for training and testing. As a result, 80% of lead models were used for the training data while the testing data was composed of the remaining 20% of lead models. This procedure was repeated five times such that all data were used as a test set (i.e., five-fold cross-validation).

The simple neural network architecture was implemented in Python 3.6 and Keras 2.3.1 with TensorFlow backend. In alternative implementations, machine learning environments other than a neural network may be used. Other Python libraries including Scikit-learn 0.21.2 were also used to support data processing. In alternative implementations, different software may be used. The algorithm was trained to predict maximum 1 g-averaged SAR ($1gSAR_{max}$) at the tips of implanted leads using the $E_{tan}$ values associated with the extracranial region of the leads. Model performance was evaluated with the mean squared error (MSE) and the correlation coefficient (R). Additionally, predicted SAR values from the deep learning approach were compared to the ground-truth SAR values from the full-wave EM simulations. Training loss per training epoch was collected and analyzed to assess potential overfitting to the data. To further explore this possibility, a five-fold cross validation schema was used to evaluate the model's training and unique testing on a unique test dataset for five different models using the dataset. A preliminary hyperparameter optimization was performed to determine the optimal number of hidden layers and nodes per hidden layer. Hyperparameter optimization was conducted using a GridSearchCV method with five-fold cross validation on the training dataset of the first fold. Once the optimal hyperparameter values were identified, these values were frozen and applied to the four remaining unique training and testing datasets in the five-fold cross validation schema.

Figure 4:
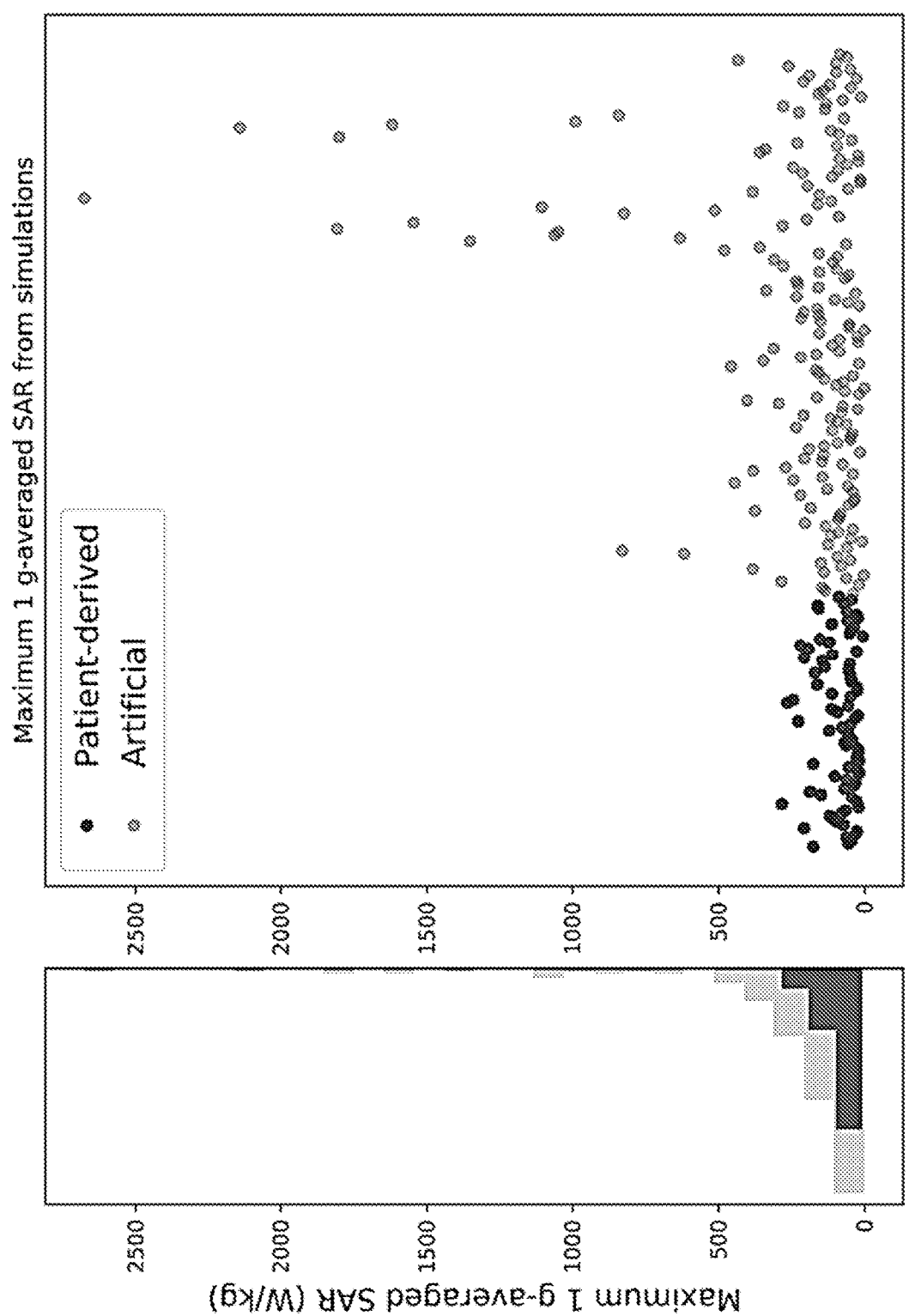
FIG. 4 depicts the distribution of maximum 1 g-averaged SAR ($1gSAR_{max}$) at the lead-tip of 260 different lead trajectories from EM simulations in accordance with an illustrative embodiment.

Based on the above-described testing scenario, RF-induced heating was quantified with $1gSAR_{max}$, which occurred at the lead-tip for all models. The $1gSAR_{max}$ ranged from 1.6 W/kg to 2674.6 W/kg across patient-derived and artificial lead trajectories, with leads with artificial trajectories demonstrating significantly higher $1gSAR_{max}$ (247.4±388.9 W/kg) than leads with patient-derived trajectories (86.5±65.3 W/kg). The highest $1gSAR_{max}$ for an artificial trajectory was 2674.6 W/kg compared to 283.4 W/kg for a patient-derived trajectory. Thus, inclusion of artificial trajectories extended the range of SAR values in the dataset to illustrate worst-case scenario heating. FIG. 4 depicts the distribution of maximum 1 g-averaged SAR at the lead-tip of 260 different lead trajectories from EM simulations in accordance with an illustrative embodiment.

Figure 5:
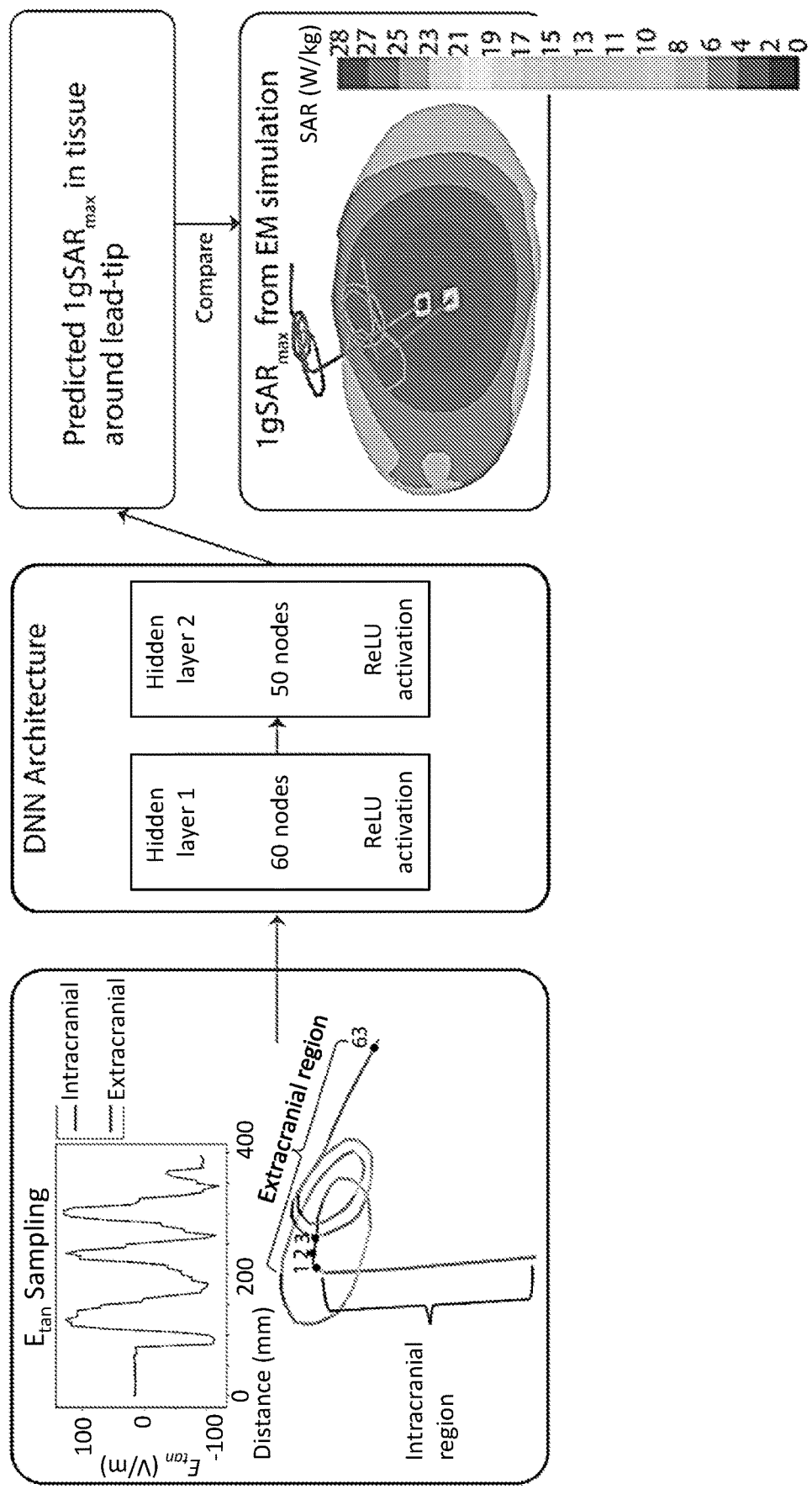
FIG. 5 depicts the architecture for the proposed deep learning algorithm in accordance with an illustrative embodiment.

The above-discussed study demonstrates that even a simplistic deep neural network architecture or other machine learning system can be beneficial for predicting RF heating as indicated by SAR. FIG. 5 depicts the architecture for the proposed deep learning algorithm in accordance with an illustrative embodiment. As shown, the model is a fully connected feed-forward neural network that includes two hidden layers with 60 and 50 nodes in the first and second layer, respectively, and an output layer. In the analysis, 63 $E_{tan}$ values along the extracranial region of the leads served as the inputs with the output being the $1gSAR_{max}$ at the lead-tip. Rectified linear unit (ReLU) activation functions were used in the hidden layers while a linear activation function was used in the output layer. Additionally, optimal parameters included 1000 epochs and a batch size of 200. Network weights were determined with an Adam optimization routine.

Figure 6A:
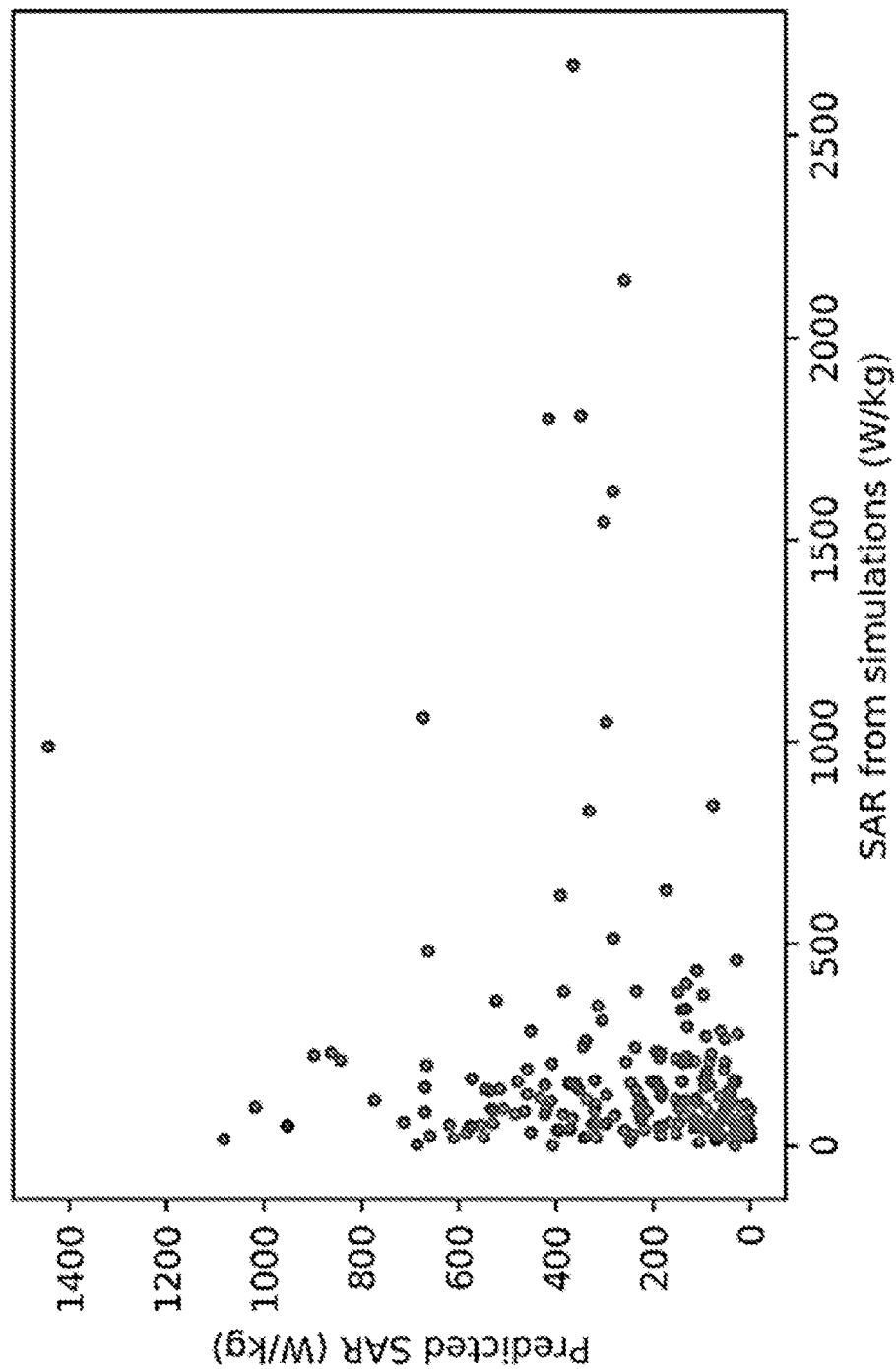
FIG. 6A shows results from a training set size of 20% in accordance with an illustrative embodiment.
Figure 6B:
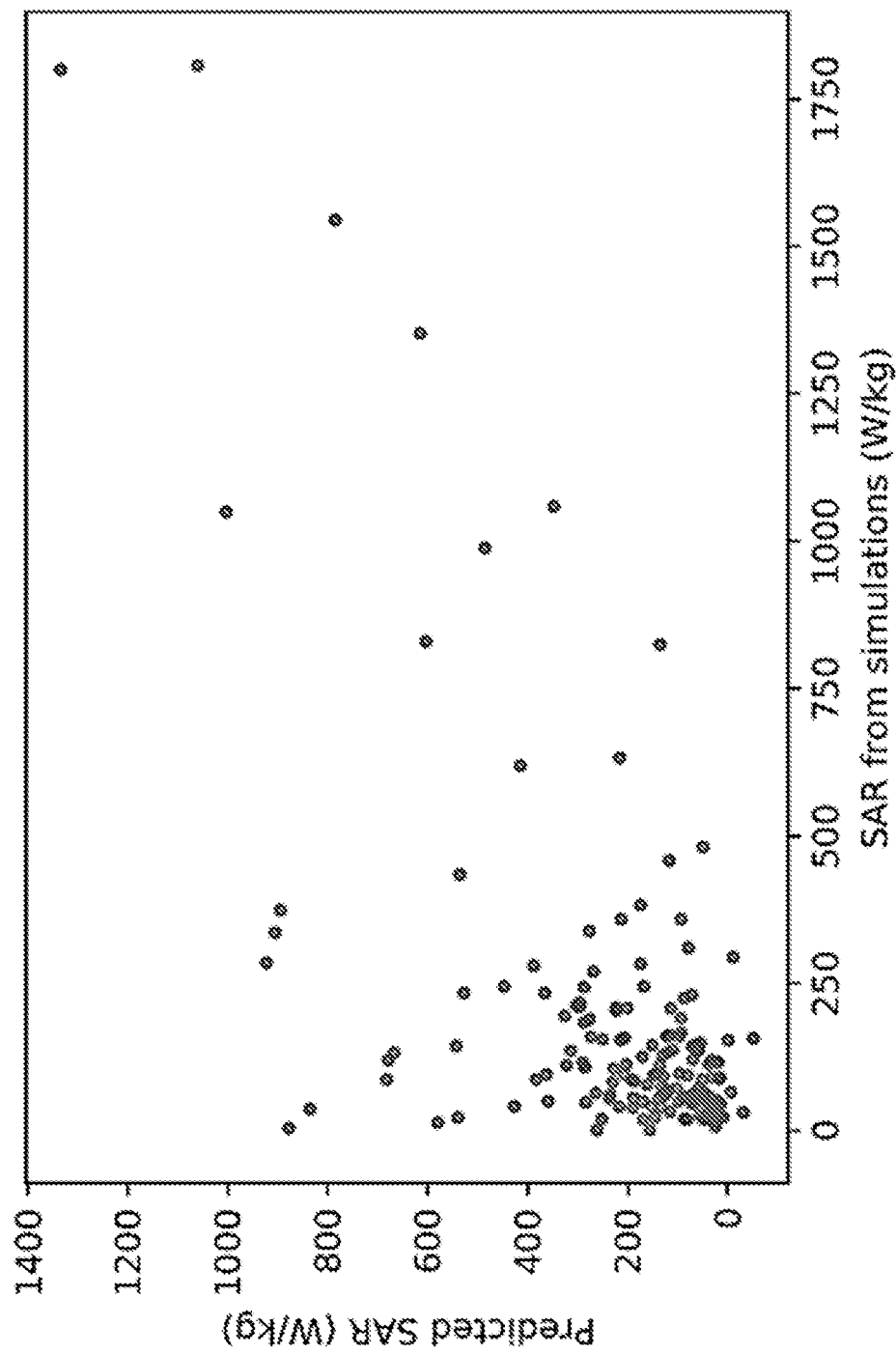
FIG. 6B shows results from a training set size of 40% in accordance with an illustrative embodiment.
Figure 6C:
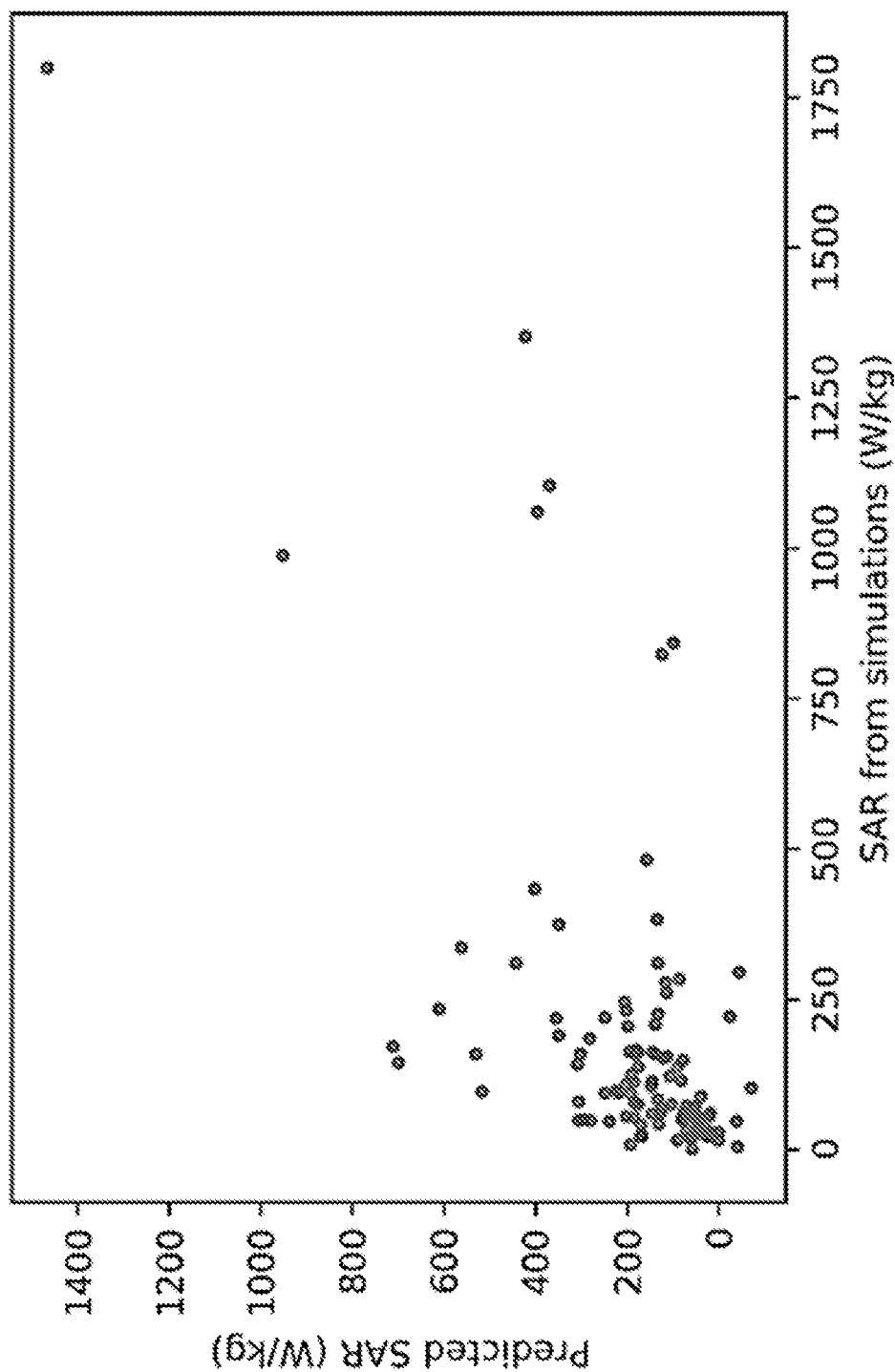
FIG. 6C shows results from a training set size of 60% in accordance with an illustrative embodiment.
Figure 6D:
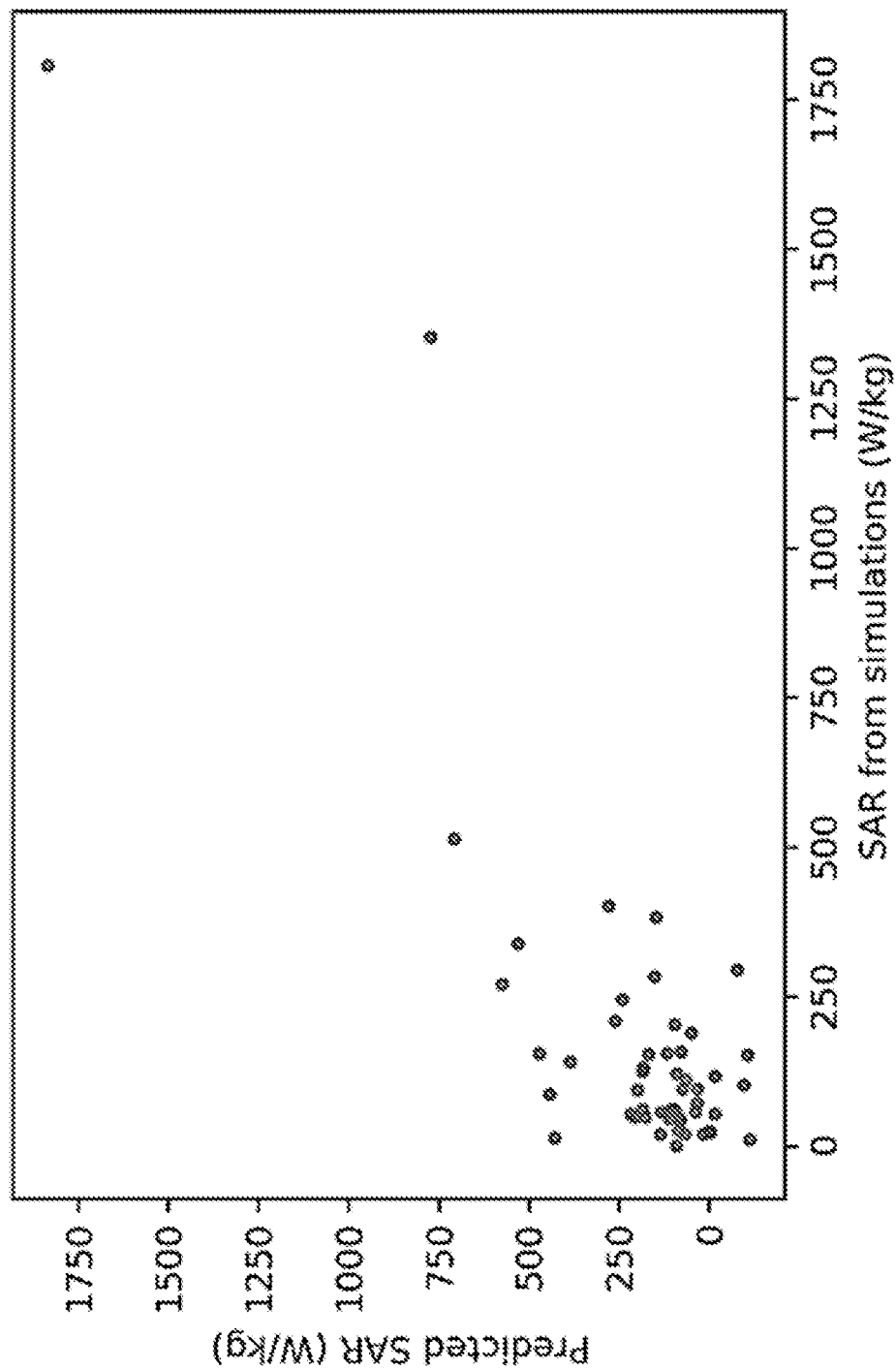
FIG. 6D shows results from a training set size of 80% in accordance with an illustrative embodiment.

Additionally, the effect of training size on model prediction performance was investigated, and the following training set sizes were evaluated: 20%, 40%, 60%, and 80%. FIG. 6A shows results from a training set size of 20% in accordance with an illustrative embodiment. FIG. 6B shows results from a training set size of 40% in accordance with an illustrative embodiment. FIG. 6C shows results from a training set size of 60% in accordance with an illustrative embodiment. FIG. 6D shows results from a training set size of 80% in accordance with an illustrative embodiment. As shown, increasing the training size from 40% of lead models to 80% of lead models led to improved predictions of $1gSAR_{max}$ during testing (R=0.55 to R=0.83).

Figure 7:
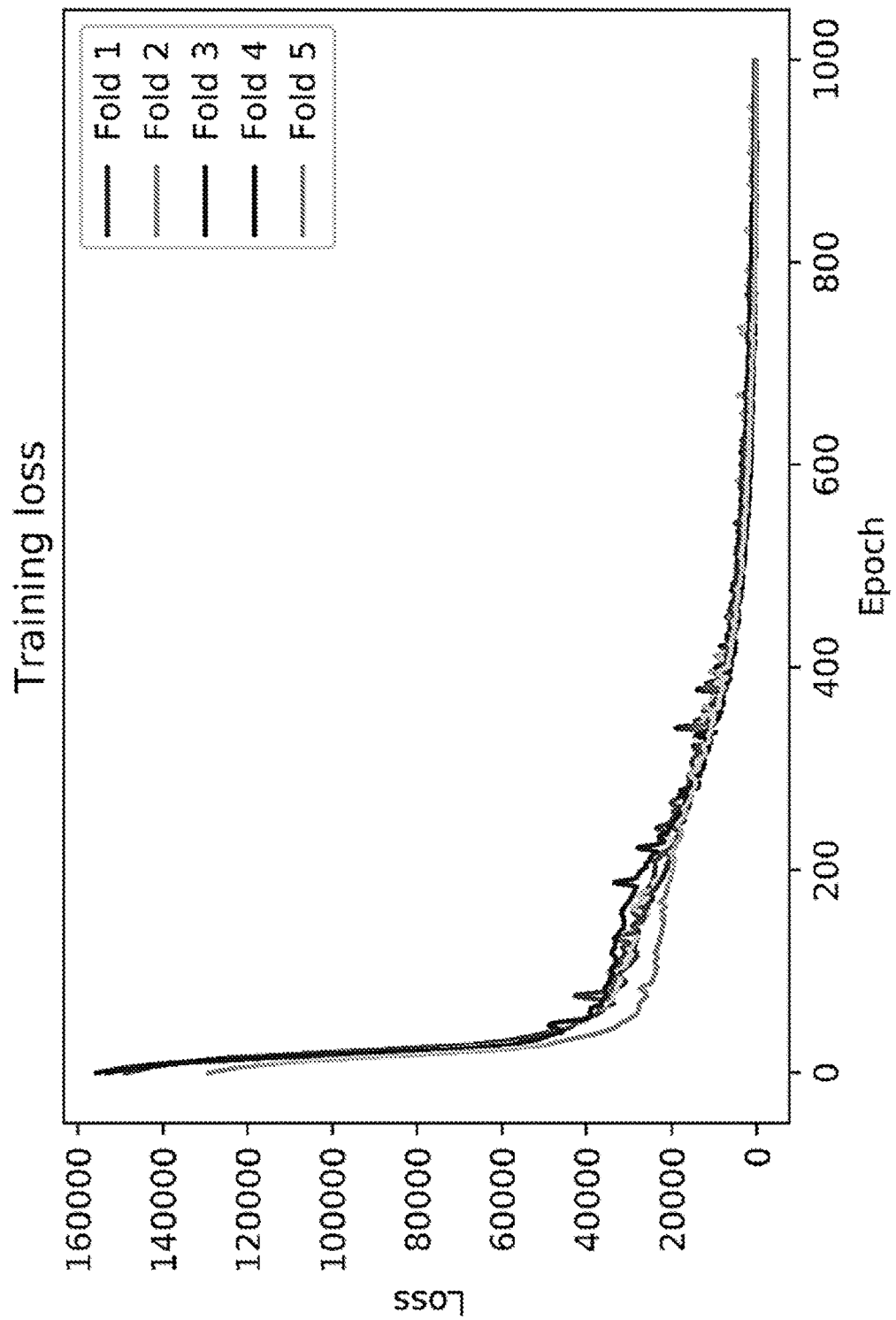
FIG. 7 depicts the training history, indicated by the mean squared error, for all folds of five-fold cross-validation in accordance with an illustrative embodiment.
Figure 8:
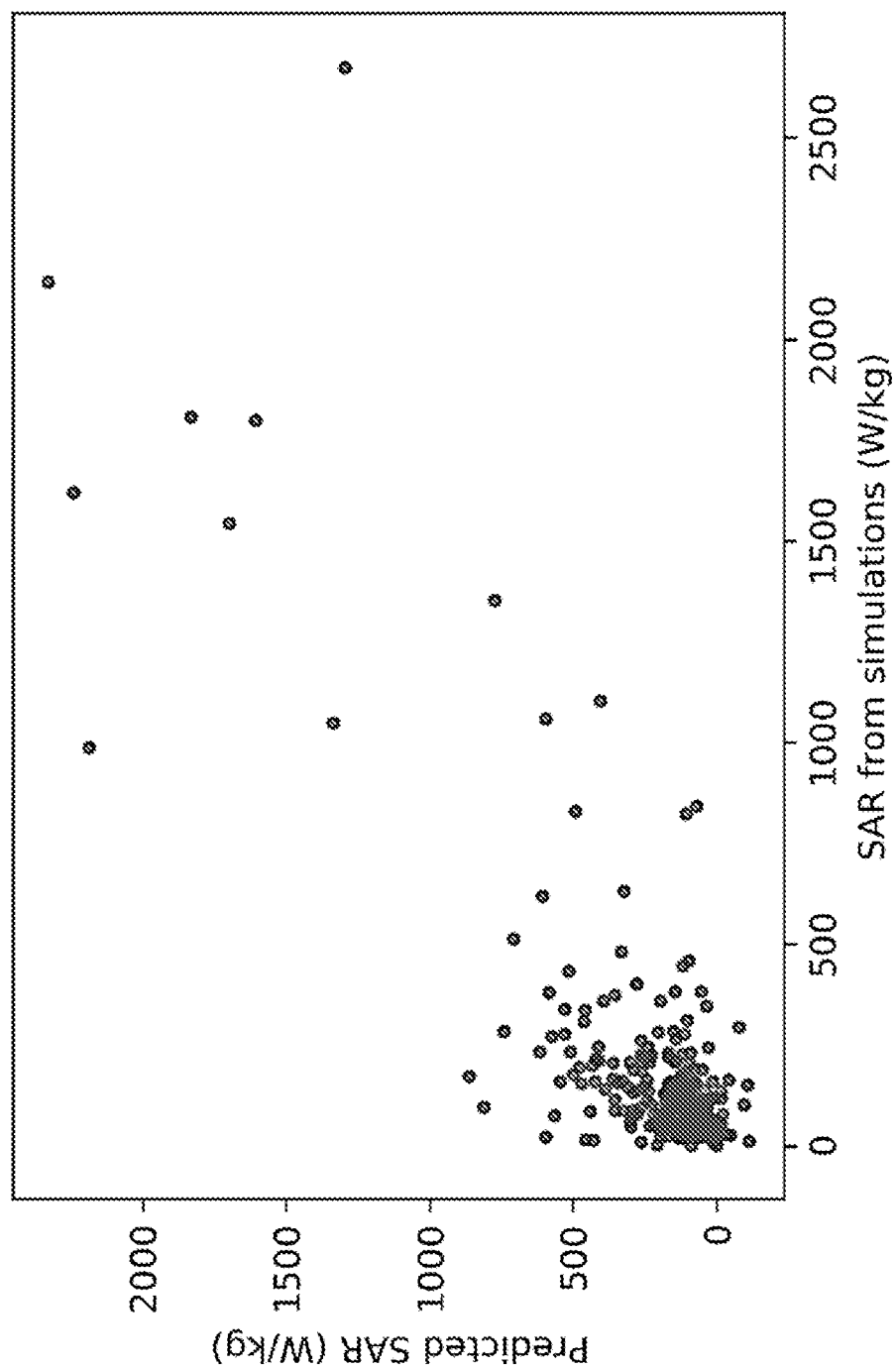
FIG. 8 demonstrates the performance of the deep network for predicting maximum SAR from the testing datasets based on the 63 $E_{tan}$ values per lead trajectory in accordance with an illustrative embodiment.

Using the proposed algorithm, training of the deep network model was completed within minutes, and predictions were generated within seconds. After 1000 epochs of training during each fold of five-fold cross validation, the deep learning algorithm performed with an average MSE=282 $W^2/kg^2$, as shown in FIG. 7. Specifically, FIG. 7 depicts the training history, indicated by the mean squared error, for all folds of five-fold cross-validation in accordance with an illustrative embodiment. FIG. 8 demonstrates the performance of the deep network for predicting maximum SAR from the testing datasets based on the 63 $E_{tan}$ values per lead trajectory in accordance with an illustrative embodiment. In FIG. 8, predicted $1gSAR_{max}$ values from testing of the DL algorithm are plotted against the ground-truth $1gSAR_{max}$ values from EM simulations. As shown, the deep learning algorithm is able to recognize high and low SAR producing trajectories during testing. Testing performance is indicated with an average R=0.73 and an average mean-squared error (MSE)=48,364 $W^2/kg^2$ across all folds of the five-fold cross-validation schema.

In another analysis of the proposed algorithm and system, the inventors generated 600 clinically relevant lead trajectories based on evaluation of thoracic X-ray photographs of patients with cardiac pacemakers and defibrillators. From these, 300 trajectories corresponded to cases where the implanted pulse generator (IPG) was in the left pectoral region and 300 trajectories corresponded to the IPG in the right pectoral region. All trajectories were 58 cm long, similar to typical active fixation leads (e.g., Medtronic 5076, Medtronic 4076) and passive fixation leads (e.g., Medtronic 4074) for cardiac pacing. Lead trajectories were generated in Rhino3D®, using the Grasshopper module, and an ANSYS human body model (ANSYS Human Body Model V3) was used for anatomical guidance. In alternative embodiments, different lead lengths and/or software may be used.

Figure 9B:
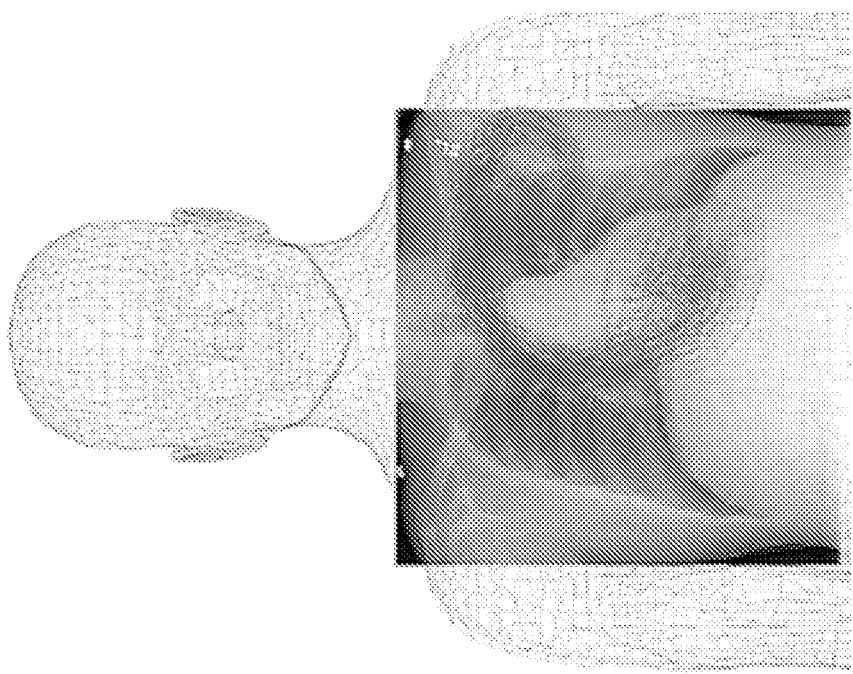
FIG. 9B is an x-ray image of a patient with cardiovascular implantable electronic devices overlaid on a human body model and manual trajectories with IPGs on the right in accordance with an illustrative embodiment.
Figure 9A:
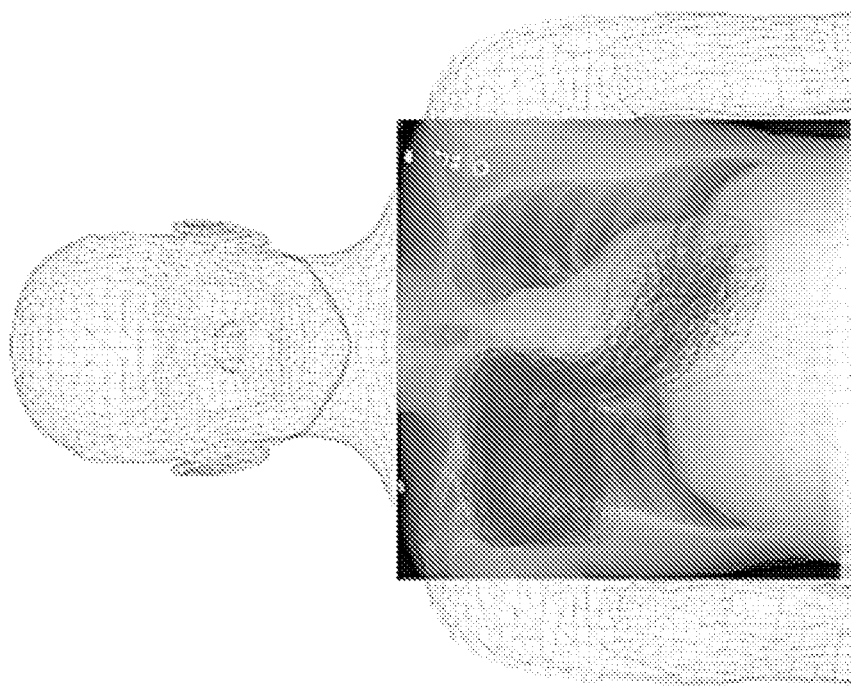
FIG. 9A is an x-ray image of a patient with cardiovascular implantable electronic devices overlaid on a human body model and manual trajectories with implantable pulse generators (IPGs) on the left in accordance with an illustrative embodiment.

The trajectories were designed starting from the assumptive position of IPG in left or right pectoral region and followed a path through subclavian vein or superior vena cava to the heart. To generalize the model for different body forms, the size of heart was enlarged by 50%. From an inspection of radiographic images from patients, as well as reports from other groups, it was found that lead pathways in large veins had minor differences whereas the pathway of the distal part of the lead and the position of the lead tip had remarkable variability, virtually covering the entire heart. These guidelines were incorporated in the algorithm that generated lead trajectories, as shown in FIG. 9. Specifically, FIG. 9A is an x-ray image of a patient with cardiovascular implantable electronic devices overlaid on a human body model and manual trajectories with IPGs on the left in accordance with an illustrative embodiment. FIG. 9B is an x-ray image of a patient with cardiovascular implantable electronic devices overlaid on a human body model and manual trajectories with IPGs on the right in accordance with an illustrative embodiment.

Finite element simulations were performed to calculate the local SAR at tips of implanted lead models during MRI RF exposure using a computing system. A model of a lowpass 16-rung birdcage coil (diameter=714 mm, length=470 mm) was created and tuned to its resonance frequency at 63.6 MHz corresponding to proton imaging at 1.5 T. The coil was loaded with a homogeneous human body model (ANSYS Human Body Model V3) with electric properties of average tissue ($\sigma$=0.47 S/m, $\varepsilon_r$=80). Lead trajectories were imported from Rhino3D and modeled as 90%:10% platinum-iridium wires (Pt:Ir, $\sigma$=4×10$^6$ S/m, diameter=1 mm) wrapped within urethane insulation ($\varepsilon$=3.5, diameter=2 mm) with 2 mm exposed tip. To increase the accuracy of numerical simulations around the lead tip, a 20×20×20 mm$^3$ cubic region was defined in which a fine mesh resolution was assigned (rms element length=1.57 mm). The input power of the coil was adjusted such that the spatial mean of $B_1^+$ on a transvers plane passing through the center of the coil was 2 µT. The maximum of 1 g-averaged SAR ($1gSAR_{max}$) within the high-resolution mesh region surrounding the tip was calculated using an HFSS built-in SAR module, and was used as the ground truth to train the neural network. In alternative embodiments, different lengths and simulation values may be used, and a machine learning environment other than a neural network may also be used.

Figure 10C:
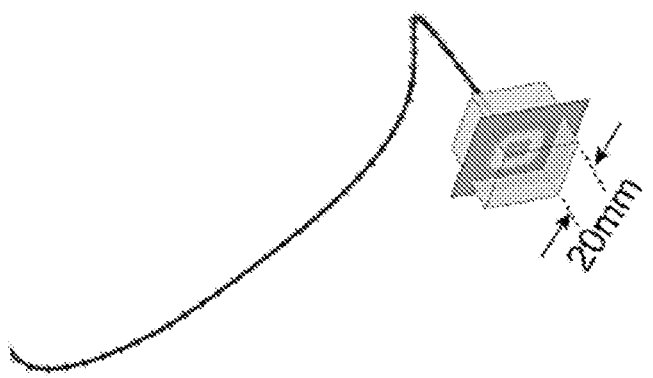
FIG. 10C shows the 1 g-averaged SAR on a central axial plane within the 20×20×20 $mm^3$ cube surrounding the exposed lead tip in accordance with an illustrative embodiment.
Figure 10B:
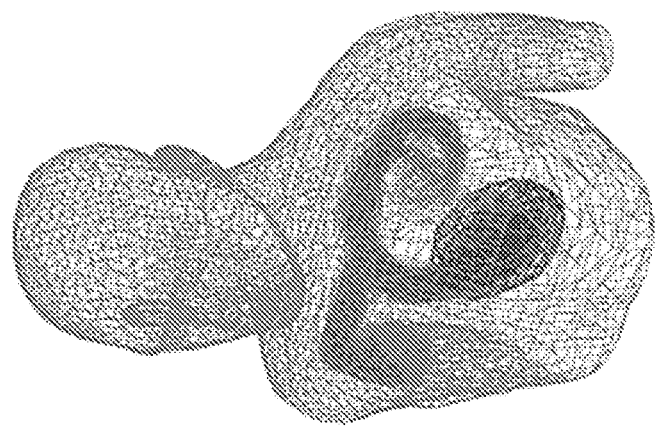
FIG. 10B depicts an overlay of 600 trajectories in the body model in accordance with an illustrative embodiment.
Figure 10A:
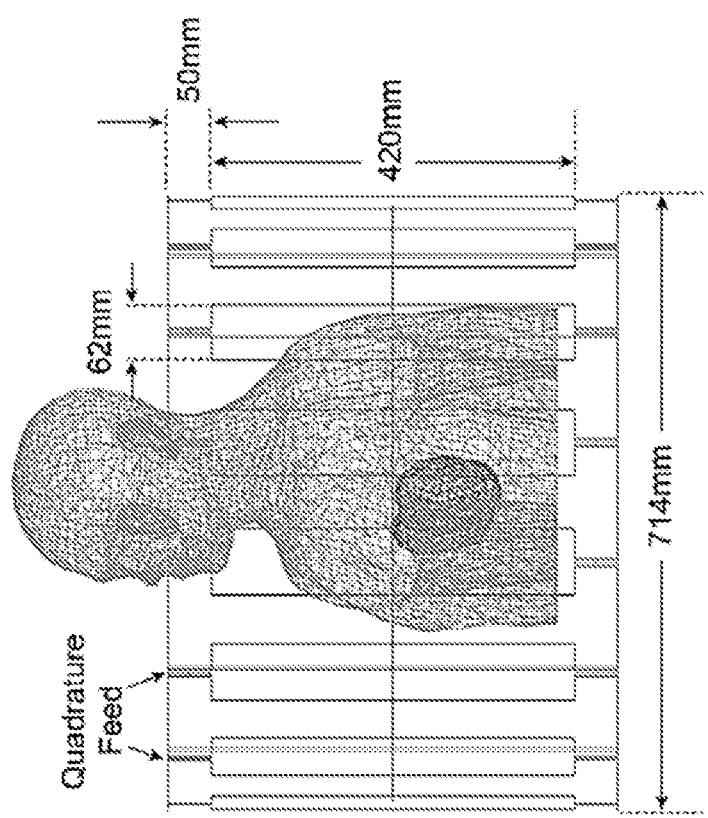
FIG. 10A depicts the simulation setup with a homogenous body model and an MRI RF coil in accordance with an illustrative embodiment.

FIG. 10A depicts the simulation setup with a homogenous body model and an MRI RF coil in accordance with an illustrative embodiment. The heart is shown to visualize the position of distal parts of leads and was not included in the FEM simulations. FIG. 10B depicts an overlay of 600 trajectories in the body model in accordance with an illustrative embodiment. FIG. 10C shows the 1 g-averaged SAR on a central axial plane within the 20×20×20 mm$^3$ cube surrounding the exposed lead tip in accordance with an illustrative embodiment.

The total data for 600 trajectories was divided into a training set (64%), a validation set (16%), and a testing set (20%). A feedforward neural network was designed which took coordinates of 116 points sampled along length of each lead as input and predicted $1gSAR_{max}$ in the tissue surrounding the lead tip. The network contained one input layer, five hidden layers with dropouts, and one output layer. The size of input data was first compressed to 348×1 from 116×3 by concatenation to fit the neural network. Fully connected hidden layers activated by a ReLU function were used to learn the nonlinear relationship between lead coordinates and $1gSAR_{max}$. To reduce overfitting and improve generalization error, a dropout was introduced for each hidden layer. Additionally, the output layer linearly regressed the predicted $1gSAR_{max}$ as one scaler.

Figure 11A:
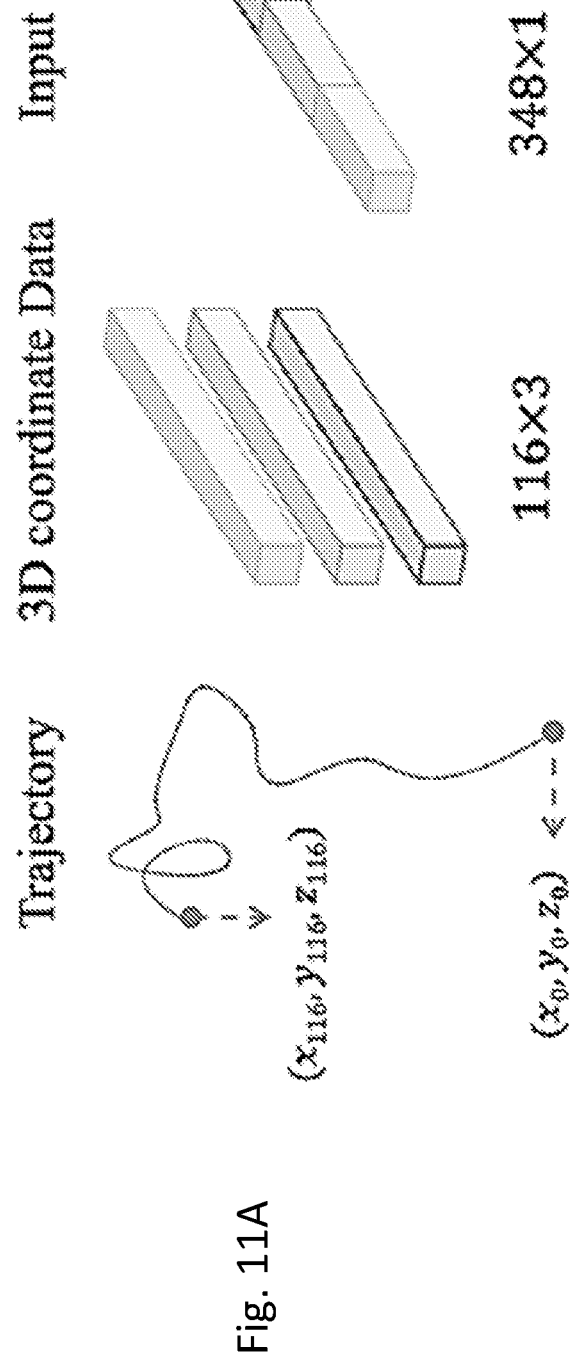
FIG. 11A shows the concatenation of 3D coordinates in accordance with an illustrative embodiment.
Figure 11B:
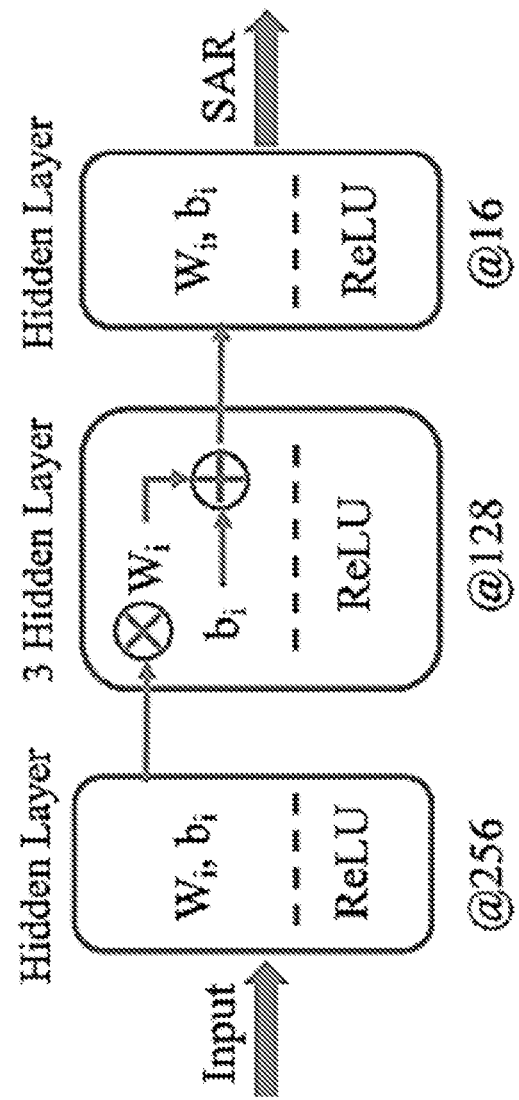
FIG. 11B depicts the structure of the feedforward neural network in accordance with an illustrative embodiment.

Hyperparameters including number of neurons, learning rate, and dropout rate were tuned by Ray Tune, which is a Python library that accelerates hyperparameter tuning with parallelized computing. The search algorithm was Bayesian Optimization and Hyperband (BOHB), an algorithm which combines Hyperband with Bayesian optimization and is dominant in both efficiency and performance. As a result, the number of neurons of five hidden layers were optimized to 256, 128, 128, 128 and 16 respectively. FIG. 11A shows the concatenation of 3D coordinates in accordance with an illustrative embodiment. FIG. 11B depicts the structure of the feedforward neural network in accordance with an illustrative embodiment. In the network, $W_i$ and $b_i$ represent weight and bias matrices, respectively, for each layer. Weight and bias values were initialized with a normal distribution and were updated using the Adaptive Moment Estimation (Adam) gradient-based optimization algorithm. The @ symbol in FIG. 11B is followed by the number of neurons of every layer.

The simulation followed an adaptive mesh scheme where an initial mesh with a user-defined resolution (20 mm in human body, 2 mm in cubic region, 2 mm in lead insulation, 0.5 mm on the lead wire, and 10 mm on the coil) was seeded. In alternative simulations, different values may be used. Mesh resolution was enhanced at each adaptive pass until the maximum difference between iterative scattering parameters fell below a predefined threshold of 0.02. In alternative embodiments, a different threshold may be used such as 0.015, 0.018, 0.022, etc. All simulations converged within 3 adaptive passes. FIG. 12 includes a table that gives the mesh statistics for a representative simulation in accordance with an illustrative embodiment. Each simulation took around 80 minutes to complete on a DELL PowerEdge R740 server with 1.5 TB memory and 2xXenon(R) Gold 6140 CPUs, each having 18 processing cores. In alternative implementations, a different computer and/or different computing specifications may be used.

Figure 13:
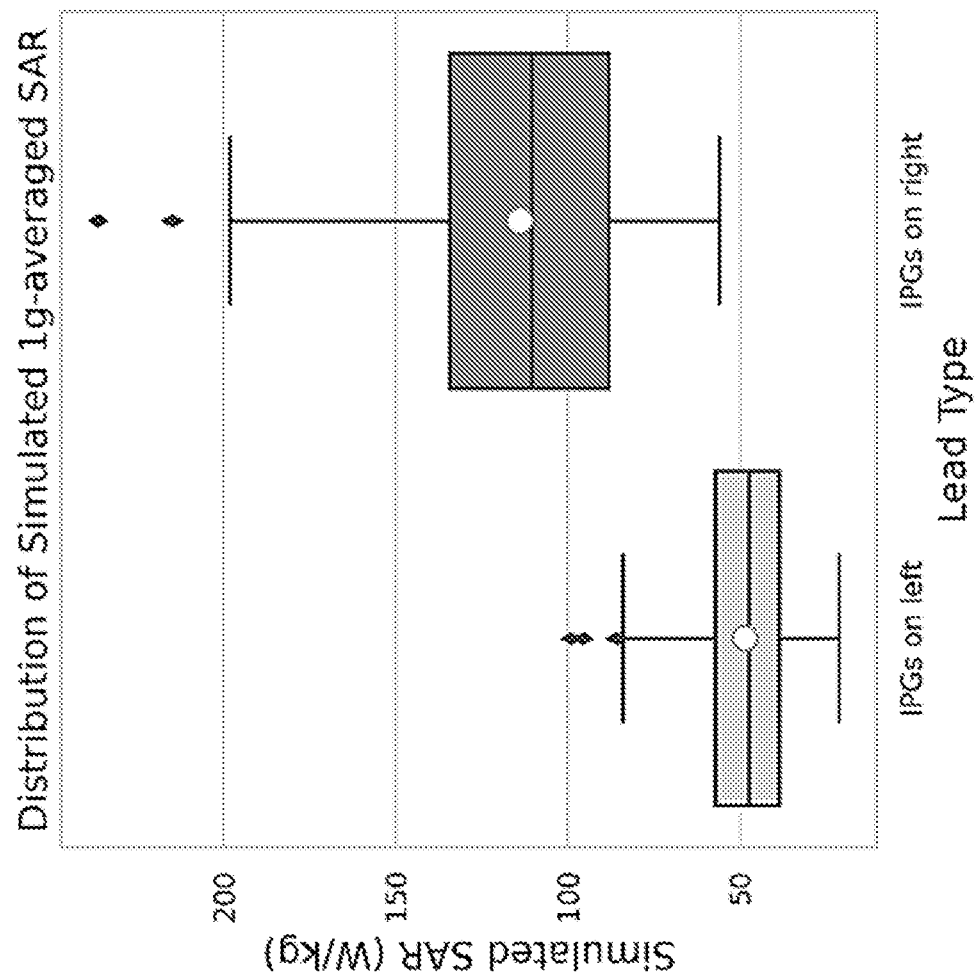
FIG. 13 depicts the distribution of the normalized $1gSAR_{max}$ values for trajectories with IPGs in left and right pectoral regions in accordance with an illustrative embodiment.

FIG. 13 depicts the distribution of the normalized $1gSAR_{max}$ values for trajectories with IPGs in left and right pectoral regions in accordance with an illustrative embodiment. The $1gSAR_{max}$ was 48.67±14.49 W/kg and 113.97±32.28 W/kg for trajectories with IPG in left and right pectoral regions, respectively. A one-tail t-test showed the $1gSAR_{max}$ of trajectories with IPG in right side to be significantly greater ($p=3\times10^{-114}$) than SAR of trajectories with IPG in the left side.

Figure 14:
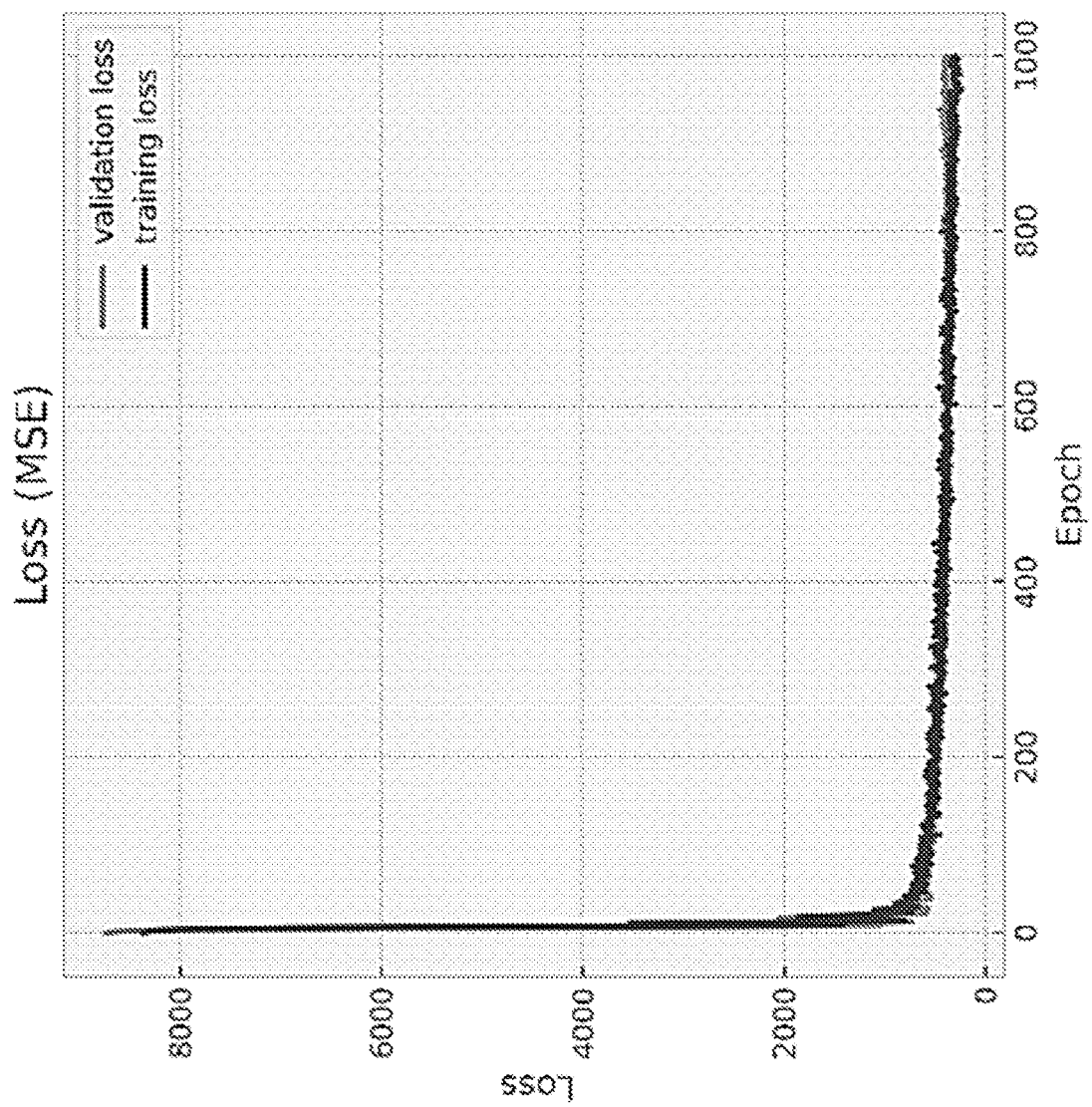
FIG. 14 depicts training loss and validation loss with the increasing epochs in accordance with an illustrative embodiment.

The mean squared error (MSE) was chosen to be the optimization target during training. Both training and validation losses substantially decreased within 100 epochs and converged to ~380 W)/kg) after 700 epochs. FIG. 14 depicts training loss and validation loss with the increasing epochs in accordance with an illustrative embodiment. After the decrease in training and validation losses, the network started to overfit the training data as the gap between validation loss and training loss increased. Therefore, the number of epochs for training was set to 700. On the test dataset, the Root Mean Squared Error (RMSE) is 14.5 W/kg, and trajectories with IPGs in left and right pectoral regions were 9.2 W/kg and 18.3 W/kg, respectively.

Figure 15:
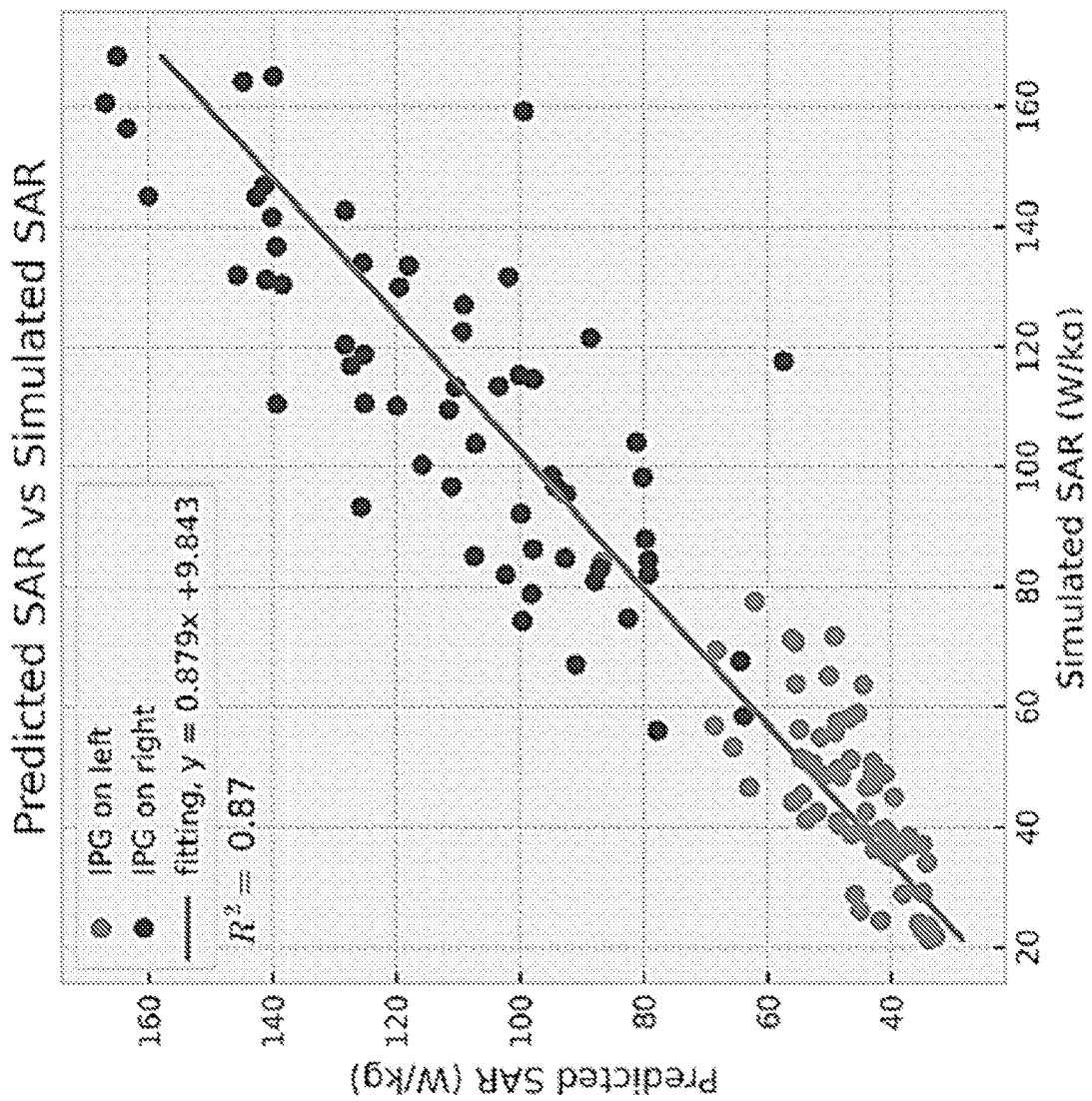
FIG. 15 shows the comparison of simulated and predicted $1gSAR_{max}$ resulting in a high coefficient of determination ($R^2$) score of 0.87 in accordance with an illustrative embodiment.

FIG. 15 shows the comparison of simulated and predicted $1gSAR_{max}$ resulting in a high coefficient of determination ($R^2$) score of 0.87 in accordance with an illustrative embodiment. The feedforward network performed better in predicting heating of trajectories with IPGs in left than that in right, but the latter still maintained enough linearity in a wider SAR range with few outlier predictions.

Figure 16:
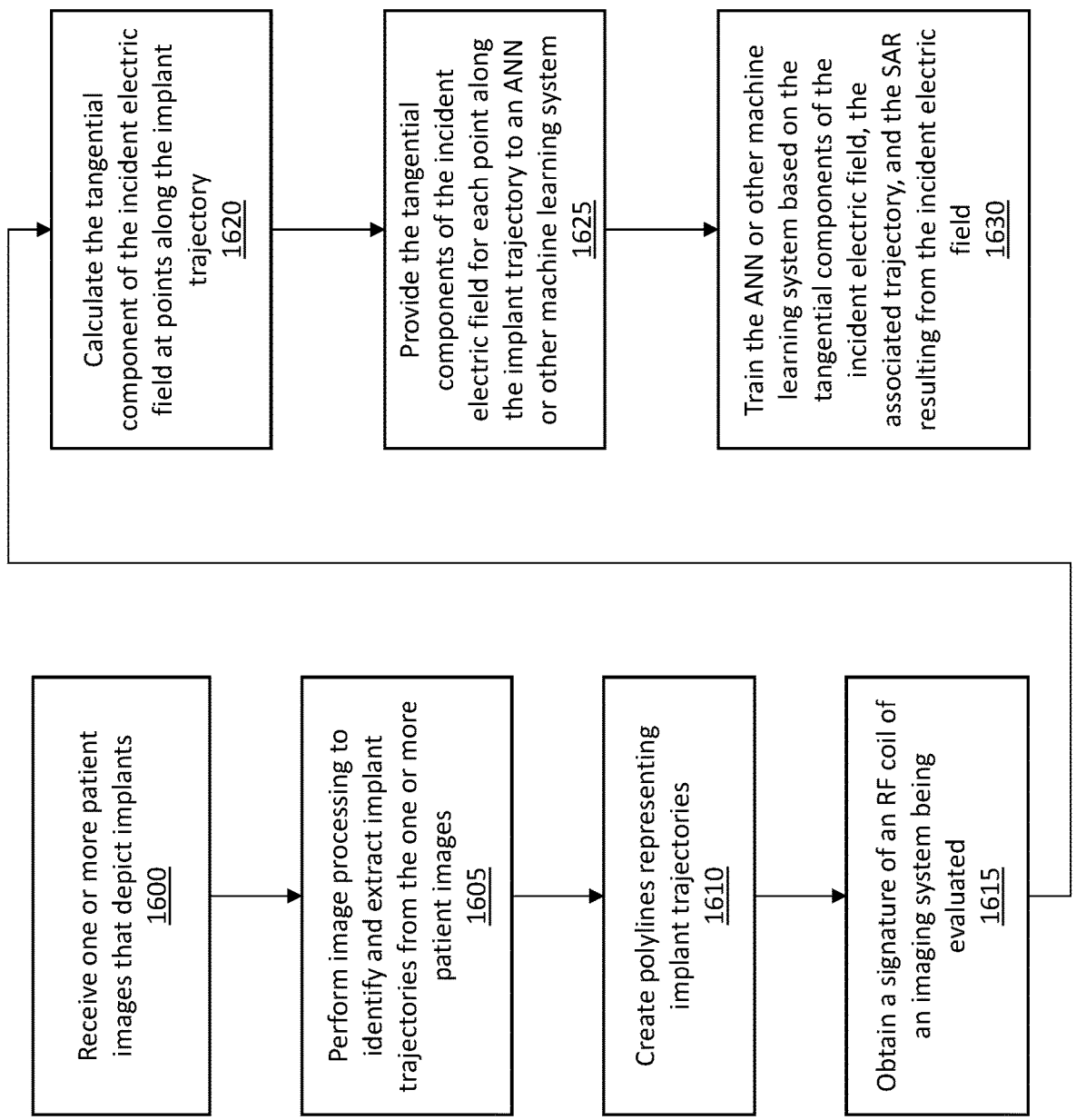
FIG. 16 is a flow diagram that depicts operations performed by a system to generate an artificial neural network or other machine learning system to predict local specific absorption rate (SAR) of an implant in accordance with an illustrative embodiment.

FIG. 16 is a flow diagram that depicts operations performed by a system to generate an artificial neural network or other machine learning system to predict local SAR of an implant in accordance with an illustrative embodiment. In alternative embodiments, fewer, additional, and/or different operations may be performed. Additionally, the use of a flow diagram is not meant to be limiting with respect to the order of operations performed. In an operation 1600, the system receives one or more patient images that depict implants. In an illustrative embodiment, the one or more patient images are 3D computed tomography images that depict the location and orientation of one or more implants within the patient. Alternatively, any other type of image that depicts implant orientation within the patient can be used. The one or more patient images can be received from an image database that is in communication with the system, directly from a CT imaging device that is in communication with the system, or from any other source.

In an operation 1605, the system performs image processing to identify and extract implant trajectories from the one or more patient images. In an illustrative embodiment, the system utilizes image segmentation with semi-automated thresholding to extract the implant trajectories. In alternative embodiments, a different image processing technique may be used. In an operation 1610, the system creates polylines representing the implant trajectories. In one embodiment, the system can use a finite element solver algorithm to create the polylines. Alternatively, a different type of algorithm may be used. In an operation 1615, the system obtains a signature of an RF coil of an imaging system that is to be evaluated. The signature is the value of an incident electric field generated by the RF coil of the imaging system. The signature can be obtained from stored data regarding the imaging system, by directly measuring or calculating the electric field emitted from the RF coil, or by using any other techniques known in the art.

In an operation 1620, the system calculates the tangential component of the incident electric field of the imaging system at points along the implant trajectory. For each implant, the tangential component of the electric field can be determined based on the known signature of the RF coil and the orientation at each point of interest along the trajectory of the implant. The number of points of interest along the trajectory of the implant can be 10, 30, 50, 80, 100, 150, etc., and can vary depending on the embodiment. In an operation 1625, the system provides the tangential components of the incident electric field for each point along the implant trajectory as inputs to an ANN or other machine learning system. In an operation 1630, the system trains the ANN or other machine learning system based on the tangential components of the incident electric field, the associated trajectory, and the SAR resulting from the incident electric field. The SAR resulting from the incident electric field can be determined using finite element simulations. In one embodiment, a maximum 1 g-averaged SAR is calculated in the tissue at the exposed tip of each implant and used as a training output.

Once the system is trained, the system will be able to accurately predict the SAR that is likely to result at a given location along an implant trajectory responsive to a given incident electric field. Specifically, the system is trained to use the distribution of tangential component of the incident electric field of the imaging device along the trajectory of the implant as an input, and predict a maximum temperature rise at the tip of implant which is exposed to tissue. The system is thus able to determine a temperature rise of the implant and the tissue surrounding the implant based at least in part on the determined SAR at a given position along the implant.

Figure 17:
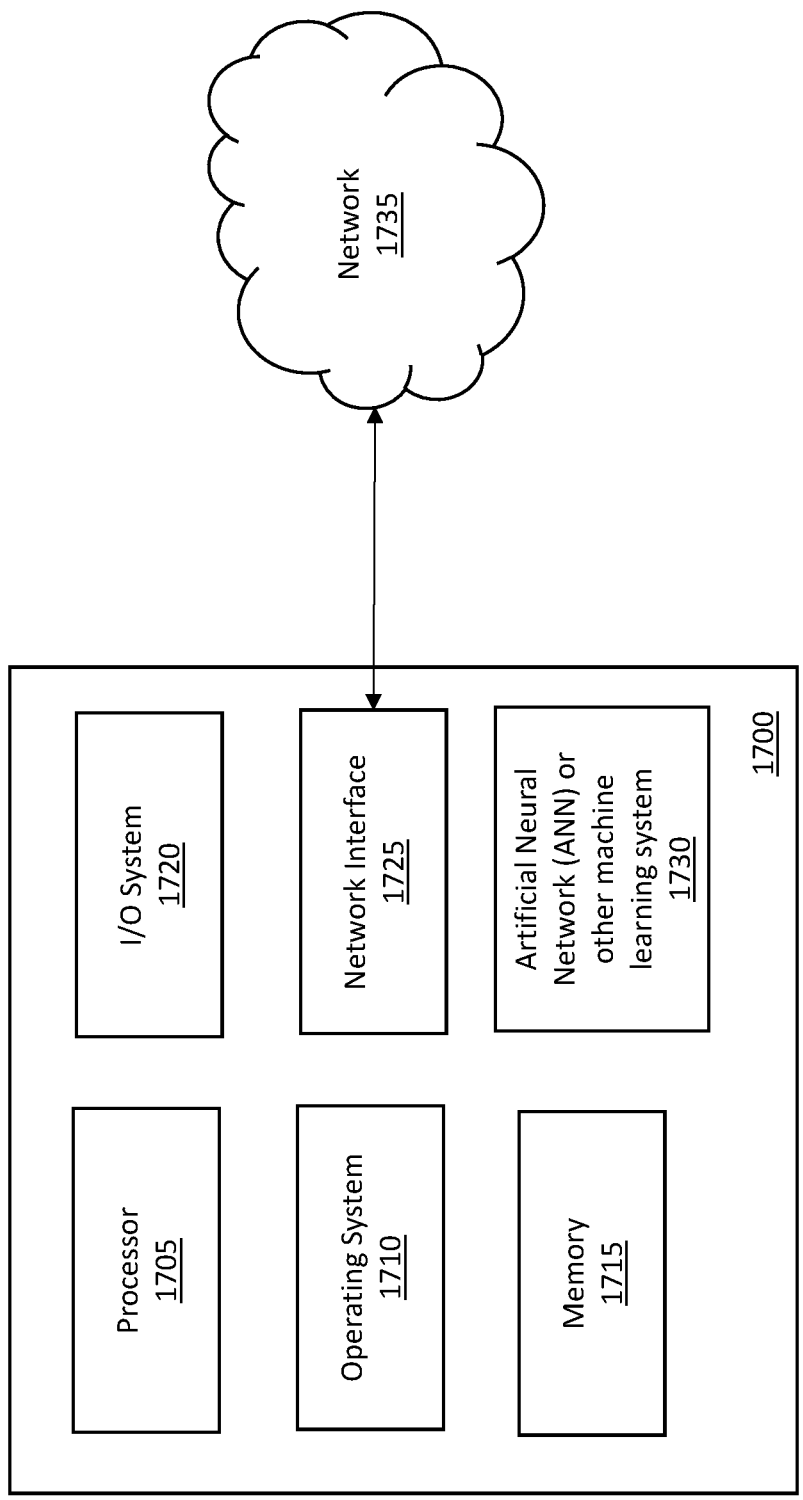
FIG. 17 is a block diagram of a computing device in communication with a network in accordance with an illustrative embodiment.

FIG. 17 is a block diagram of a computing device 1700 in communication with a network 1735 in accordance with an illustrative embodiment. The computing device 1700 includes a processor 1705, an operating system 1710, a memory 1715, an input/output (I/O) system 1720, a network interface 1725, and a deep learning artificial neural network (ANN) or other machine learning system 1730. In alternative embodiments, the computing device 1700 may include fewer, additional, and/or different components. The components of the computing device 1700 communicate with one another via one or more buses or any other interconnect system. The computing device 1700 can be any type of networked computing device such as a laptop computer, desktop computer, smart phone, tablet, dedicating computing sub-system, etc.

The processor 1705 can be any type of computer processor known in the art, and can include a plurality of processors and/or a plurality of processing cores. The processor 1705 can include a controller, a microcontroller, an audio processor, a graphics processing unit, a hardware accelerator, a digital signal processor, etc. Additionally, the processor 1705 may be implemented as a complex instruction set computer processor, a reduced instruction set computer processor, an x86 instruction set computer processor, etc. The processor is used to run the operating system 1710, which can be any type of operating system.

The operating system 1710 is stored in the memory 1715, which is also used to store programs, algorithms, network and communications data, peripheral component data, the artificial neural network (ANN) or other machine learning system 1730, and other operating instructions and/or data. Alternatively, the ANN or other machine learning system 1730 may be remote from the computing device 1700. The memory 1715 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc.

The I/O system 1720 is the framework which enables users and peripheral devices to interact with the computing device 1700. The I/O system 1720 can include a mouse, a keyboard, one or more displays, a speaker, a microphone, etc. that allow the user to interact with and control the computing device 1700. The I/O system 1720 also includes circuitry and a bus structure to interface with peripheral computing devices such as imaging systems, power sources, USB devices, peripheral component interconnect express (PCIe) devices, serial advanced technology attachment (SATA) devices, high definition multimedia interface (HDMI) devices, proprietary connection devices, etc. In an illustrative embodiment, the I/O system 1720 also presents an interface to the user such that the user is able to input data and perform training of the ANN. The data can also be received from another device via the network 1735.

The network interface 1725 includes transceiver circuitry that allows the computing device 1700 to transmit and receive data to/from other devices such as remote computing systems, imaging systems, servers, websites, etc. The network interface 1725 also enables communication through the network 1735, which can be one or more communication networks. The network 1735 can include a cable network, a fiber network, a cellular network, a wi-fi network, a landline telephone network, a microwave network, a satellite network, etc. The network interface 1725 also includes circuitry to allow device-to-device communication such as Bluetooth® communication.

The ANN or other machine learning system 1730 can include software in the form of computer-readable instructions which, upon execution by the processor 1705, performs any of the various operations described herein such as receiving data, running algorithms, predicting RF heating in an implant, etc. The ANN or other machine learning system 1730 can be stored in the memory 1715 as discussed above. In an alternative implementation, the ANN or other machine learning system 1730 can be remote or independent from the computing device 1700, but in communication therewith.

Thus, described herein are methods and systems in which the tangential component of an incident electric field generated by an imaging system (e.g., MRI scanner) is used along with implant trajectory to determine the amount of heating at the tip of the implant. Machine learning is used to train a neural network to predict the heating of implants by only looking at their trajectory and position inside an MRI machine, bypassing the nearly insurmountable burden of performing full-wave electromagnetic simulations for millions of implant scenarios. The proposed methods and systems will reduce the time necessary to predict the heating of an implant from 7-24 hours to less than a minute. This is a significant improvement for medical device companies and others that develop MRI-conditional devices.

It is to be understood that any of the operations/processes described herein may be performed at least in part by a computing system that includes a processor, memory, transceiver, user interface, etc. The described operations/processes can be implemented as computer-readable instructions stored on a computer-readable medium such as the computer system memory. Upon execution by the processor, the computer-readable instructions cause the computing system to perform the operations/processes described herein, such as training and use of the ANN or other machine learning system.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A system to predict heating in implants, the system comprising:
   a memory configured to store an image of a patient, wherein the image includes a medical implant of the patient;
   a processor operatively coupled to the memory and configured to:
      determine an implant trajectory of the medical implant;
      determine a tangential component of an electric field that is incident upon the medical implant at a plurality of locations along the implant trajectory; and
      determine, based on the implant trajectory and the tangential component of the electric field at each of the plurality of locations, a specific absorption rate of radiofrequency (RF) energy associated with the medical implant.

2. The system of claim 1, wherein the image comprises a computed tomography (CT) image.

3. The system of claim 1, wherein the processor is configured to perform segmentation of the image to determine the implant trajectory.

4. The system of claim 1, wherein the plurality of locations are equally spaced along the implant trajectory.

5. The system of claim 1, wherein the medical implant comprises a wire implant, and wherein the specific absorption rate is determined for a tip of the wire implant that is embedded in tissue.

6. The system of claim 1, further comprising an imaging device in communication with the processor, and wherein the memory is configured to store a signature of the imaging device.

7. The system of claim 6, wherein the signature of the imaging device comprises an incident electric field generated by a radio frequency (RF) coil of the imaging device.

8. The system of claim 7, wherein the processor determines the tangential component of the electric field based at least in part on the signature of the imaging device.

9. The system of claim 1, wherein the processor uses a trained machine learning algorithm to determine the specific absorption rate.

10. The system of claim 1, wherein the processor is further configured to determine a temperature rise at a given location of the medical implant.

11. The system of claim 10, wherein the temperature rise is determined based at least in part on the implant trajectory and the tangential component of the electric field at the given location.

12. The system of claim 1, wherein the processor is configured to determine, based on the implant trajectory and the tangential component of the electric field at each of the plurality of locations, a maximum 1 g-averaged specific absorption rate for the medical implant.

13. The system of claim 1, wherein the processor is part of a machine learning algorithm that includes a plurality of hidden layers and an output layer.

14. The system of claim 13, wherein the plurality of hidden layers are connected hidden layers activated by a rectified linear unit function.

15. The system of claim 14, wherein each of the hidden layers includes a dropout.

16. A method for predicting heating in implants, the method comprising:
 storing, in a memory of a computing system, an image of a patient, wherein the image includes a medical implant of the patient;
 determining, by a processor operatively coupled to the memory, an implant trajectory of the medical implant;
 determining, by the processor, a tangential component of an electric field that is incident upon the medical implant at a plurality of locations along the implant trajectory; and
 determining, by the processor and based on the implant trajectory and the tangential component of the electric field at each of the plurality of locations, a specific absorption rate of radiofrequency (RF) energy associated with the medical implant.

17. The method of claim 16, wherein determining the implant trajectory includes performing segmentation of the image to extract the implant trajectory.

18. The method of claim 16, wherein determining the specific absorption rate comprises providing the implant trajectory and the tangential component of the electric field at the plurality of locations to a trained machine learning algorithm and using the trained machine learning algorithm to determine the specific absorption rate.

19. The method of claim 16, further comprising determining, by the processor, a temperature rise caused by the medical implant at a given location, wherein the temperature rise is determined based at least in part on the implant trajectory and the tangential component of the electric field at the given location.

20. The method of claim 16, further comprising determining, by the processor and based on the implant trajectory and the tangential component of the electric field at each of the plurality of locations, a maximum 1 g-averaged specific absorption rate for the medical implant.

* * * * *